(12) United States Patent
McKenna et al.

(10) Patent No.: US 8,757,166 B2
(45) Date of Patent: Jun. 24, 2014

(54) SYSTEM FOR DEFINING ENERGY FIELD CHARACTERISTICS TO ILLUMINATE NANO-PARTICLES USED TO TREAT INVASIVE AGENTS

(75) Inventors: Daniel Bernard McKenna, Vail, CO (US); Karl Michael Frantz, Broomfield, CO (US); Andrew Curtis Updegrave, Boulder, CO (US); Martin Albert Huisjen, Boulder, CO (US)

(73) Assignee: Actium BioSystems, LLC, Boulder, CO (US)

(*) Notice: Subject to any disclaimer, the term of this patent is extended or adjusted under 35 U.S.C. 154(b) by 536 days.

(21) Appl. No.: 13/012,560

(22) Filed: Jan. 24, 2011

(65) Prior Publication Data

US 2012/0190910 A1    Jul. 26, 2012

(51) Int. Cl.
*A61N 2/00* (2006.01)
*A61N 2/02* (2006.01)

(52) U.S. Cl.
CPC ........................................ *A61N 2/02* (2013.01)
USPC .............................................. 128/899; 600/9

(58) Field of Classification Search
CPC ...................................................... A61N 2/02
USPC ........................ 600/1, 2, 9, 10; 128/897–899
See application file for complete search history.

(56) References Cited

U.S. PATENT DOCUMENTS

| | | |
|---|---|---|
| 4,346,715 A | 8/1982 | Gammell |
| 6,149,576 A | 11/2000 | Gray et al. |
| 6,165,440 A | 12/2000 | Esenaliev |
| 6,238,421 B1 | 5/2001 | Gunther et al. |
| 6,423,056 B1 | 7/2002 | Ishikawa et al. |
| 6,530,944 B2 | 3/2003 | West et al. |
| 6,961,620 B2 | 11/2005 | Rioux et al. |
| 7,133,725 B2 | 11/2006 | Stirbl et al. |
| 7,174,217 B2 | 2/2007 | Rioux et al. |
| 7,623,908 B2 | 11/2009 | Boppart et al. |
| 7,819,835 B2 | 10/2010 | Landy et al. |
| 7,842,281 B2 | 11/2010 | Haik et al. |
| 7,951,061 B2 | 5/2011 | Foreman et al. |

(Continued)

FOREIGN PATENT DOCUMENTS

WO    WO-2010139386 A1    12/2010

OTHER PUBLICATIONS

Silica Nanoparticle Size Influencs the Structure and Enzymatic Activity of Adsorbed Lysozyme. Vertegel AA, Siegel RW, Dordick JS. Langmuir 2004, 20, 6800-6807.*

(Continued)

*Primary Examiner* — Christine Matthews
*Assistant Examiner* — Joshua D Lannu
(74) *Attorney, Agent, or Firm* — Patton Boggs LLP

(57) ABSTRACT

The Invasive Agent Treatment System incorporates the pairing of energy fields with nano-particles to cause a thermal effect in the nano-particles, which thermal effect is transmitted into the biological cells of the invasive agent. The energy fields are derived from at least one or a combination of the following: an electric field, a magnetic field, an electromagnetic field (EM), an acoustic field, and an optical field. The Invasive Agent Treatment System provides the necessary coordination among the characteristics of the nano-particles, concentration of nano-particles, duration of treatment, and applied fields to enable the generation of precisely crafted fields and their application in a mode and manner to be effective with a high degree of accuracy.

17 Claims, 34 Drawing Sheets

(56) References Cited

U.S. PATENT DOCUMENTS

| | | |
|---|---|---|
| 2001/0012912 A1 | 8/2001 | Feucht |
| 2002/0091377 A1 | 7/2002 | Anderson et al. |
| 2002/0193784 A1 | 12/2002 | McHale et al. |
| 2005/0015049 A1 | 1/2005 | Rioux et al. |
| 2005/0059852 A1 | 3/2005 | Rioux et al. |
| 2005/0215988 A1 | 9/2005 | Altshuler et al. |
| 2005/0249817 A1 | 11/2005 | Haik et al. |
| 2006/0015098 A1 | 1/2006 | Rioux et al. |
| 2006/0142748 A1 | 6/2006 | Foreman et al. |
| 2006/0269612 A1 | 11/2006 | Xiang et al. |
| 2007/0010702 A1 | 1/2007 | Wang et al. |
| 2007/0135373 A1 | 6/2007 | Li et al. |
| 2007/0258889 A1 | 11/2007 | Douglas et al. |
| 2008/0103355 A1 | 5/2008 | Boyden et al. |
| 2008/0114429 A1 | 5/2008 | Nagano et al. |
| 2008/0300571 A1 | 12/2008 | LePivert |
| 2008/0319375 A1 | 12/2008 | Hardy |
| 2009/0043256 A1 | 2/2009 | Landy et al. |
| 2009/0054722 A1 | 2/2009 | Sugano et al. |
| 2009/0076496 A1 | 3/2009 | Azure |
| 2009/0076502 A1 | 3/2009 | Azure et al. |
| 2009/0157069 A1 | 6/2009 | Tom et al. |
| 2009/0220968 A1 | 9/2009 | Issadore et al. |
| 2009/0287036 A1 | 11/2009 | Shapiro et al. |
| 2010/0016783 A1 | 1/2010 | Bourke, Jr. et al. |
| 2010/0056643 A1 | 3/2010 | Bachynsky et al. |
| 2010/0099941 A1 | 4/2010 | Haik et al. |
| 2010/0160483 A1 | 6/2010 | Vogt et al. |
| 2010/0204674 A1 | 8/2010 | Forbes et al. |
| 2010/0222774 A1 | 9/2010 | Hegg et al. |
| 2010/0292564 A1* | 11/2010 | Cantillon Murphy ........ 600/411 |
| 2010/0310636 A1 | 12/2010 | Sharma et al. |
| 2011/0104305 A1 | 5/2011 | Day et al. |
| 2011/0125232 A1 | 5/2011 | Landy et al. |
| 2011/0137230 A1 | 6/2011 | Altshuler et al. |
| 2011/0177153 A1 | 7/2011 | Zhu |
| 2012/0259154 A1 | 10/2012 | Hong et al. |
| 2013/0053619 A1 | 2/2013 | McKenna et al. |
| 2013/0053620 A1 | 2/2013 | Susedik et al. |

OTHER PUBLICATIONS

Barnes et al.; *Bioengineering and Biophysical Aspects of Electromagnetic Fields*, Third Edition, 2007; p. 298 and 299.
International Search Report in corresponding PCT Application No. PCT/US11/68114 dated Apr. 19, 2012, 3 pages.
International Search Report in corresponding PCT Application No. PCT/US11/68116 dated May 8, 2012, 3 pages.
International Search Report in corresponding PCT Application No. PCT/US11/68134 dated May 8, 2012, 3 pages.
International Search Report in corresponding PCT Application No. PCT/US11/68142 dated May 4, 2012, 3 pages.
International Search Report in corresponding PCT Application No. PCT/US11/68146 dated May 2, 2012, 3 pages.
International Search Report in corresponding PCT Application No. PCT/US11/68154 dated May 3, 2012, 3 pages.
In the US Patent and Trademark Office U.S. Appl. No. 13/012,527 Non-Final Office Action dated Apr. 29, 2013, 13 pages.
In the US Patent and Trademark Office U.S. Appl. No. 13/012,572 Non-Final Office Action dated May 23, 2013, 12 pages.
International Search Report in corresponding PCT Application No. PCT/US12/51763 dated Oct. 22, 2012, 3 pages.
International Search Report in corresponding PCT Application No. PCT/US12/51765 dated Oct. 22, 2012, 3 pages.
In the US Patent and Trademark Office U.S. Appl. No. 13/012,509 Non-Final Office Action dated Mar. 21, 2014, 6 pages.
In the US Patent and Trademark Office U.S. Appl. No. 13/012,527 Final Office Action dated Dec. 26, 2013, 11 pages.
In the US Patent and Trademark Office U.S. Appl. No. 13/012,539 Non-Final Office Action dated Jan. 16, 2014, 6 pages.
In the US Patent and Trademark Office U.S. Appl. No. 13/012,572 Final Office Action dated Dec. 19, 2013, 10 pages.
In the US Patent and Trademark Office U.S. Appl. No. 13/590,515 Non-Final Office Action dated Apr. 29, 2014, 16 pages.

* cited by examiner

TARGET PARTICLE DATABASE

| Model | Geometry | Material | Dimensions | Coating | Concentration | Excitation Frequency | Response Field | Function Phase | Polarization | Field |
|---|---|---|---|---|---|---|---|---|---|---|
| 4756A | Sphere | PEG | 20 nm | None | 50 pico grms/cell | Graph A | 1000 V/m | None | Circular | EM |
| 2377V | Bar | ZincOxide | 5X20X50 nm | Antigen | 70 pico grms/cell | Graph B | 1500 V/m | Horizontal | Vertical | E, EM |
| 9736C | Cylinder | IronOxide | 10X75 nm | PEG | 85 pico grms/cell | Graph C | 1000 V/m, 15000 A/m | Vertical | Horizontal | EM, H |
| 6754Z | Ellipse | PEG Shell, Surfactant filling | 75X45 | Antigen | 65 pico grms/cell | Graph D | 2000 V/m | None | Circular | E, EM |
| 21AA | Sphere | Fe3O4 | 30nm | none | 90 picograms/cell | Graph W | 11, Three Different, Independent Methods to realize
a Fixed Temperature Rise in a given Nanoparticle

| Effect 450 | Field Type 460 | Field Dependence 470 | Temperature Dependence 480 |
|---|---|---|---|
| Magnetocaloric 451 | Magnetic 461 | Temp rise dependent on field strength 471 | On H-Field Strength 481 |
| Electrocaloric 452 | Electric 462 | Temp rise dependent on field strength 472 | On E-Field Strength 482 |
| Curie Temperature 453 | Magnetic 463 | Past the Curie Temp, an increase in field strength does not increase temperature 473 | On H-Field up to Curie Temp., then independent 483 |

Figure 15

SYSTEM FOR DEFINING ENERGY FIELD CHARACTERISTICS TO ILLUMINATE NANO-PARTICLES USED TO TREAT INVASIVE AGENTS

CROSS-REFERENCE TO RELATED APPLICATIONS

This application is related to US patent applications titled "System For Correlating Energy Field Characteristics With Target Particle Characteristics In The Application Of An Energy Field To A Living Organism For Treatment Of Invasive Agents"; "System For Correlating Energy Field Characteristics With Target Particle Characteristics In The Application Of An Energy Field To A Living Organism For Imaging Of Invasive Agents"; "System For Correlating Energy Field Characteristics With Target Particle Characteristics In The Application Of An Energy Field To A Living Organism For Imaging and Treatment Of Invasive Agents"; "System For Automatically Amending Energy Field Characteristics In The Application Of An Energy Field To A Living Organism For Treatment Of Invasive Agents"; and "Low Temperature Hyperthermia System For Therapeutic Treatment Of Invasive Agents", all filed on the same date as the present application.

FIELD OF THE INVENTION

The invention relates generally to the field of treatment of invasive agents, such as pathogens and cancers, in living organisms and, more particularly, to a system that matches input energy field characteristics, as applied to the living organism, with the characteristics of nano-particles which are infused into the living tissue that is to be treated.

BACKGROUND OF THE INVENTION

It is a problem to both accurately detect the presence of and determine the locus of invasive agents, such as pathogens and cancers (malignant neoplasm), (collectively termed "invasive agents" herein) in a living organism (ex.—human, animal), as well as treat these invasive agents. Present cancer diagnostic and treatment methods (such as chemo-therapy and radiation therapy) are imprecise and can result in damage to the living organism in order to destroy the cancer cells.

Presently, a procedure is being used where nano-particles are directed to invasive agents (cancer cells) by the use of passive and active targeting methods. The passive targeting approach uses the size and shape of the nano-particles to enhance their uptake into cancer cells while the active targeting approach uses coatings applied to the nano-particles (such as an antigen) to enable the targeted uptake of the nano-particles by only those cells, cancer cells for instance, that are susceptible to the antigen coating. The size of the nano-particles is selected to enable the cancer cells to ingest the nano-particles, yet not be able to excrete the ingested nano-particles. The nano-particles can be heated via the use of a magnetic field to raise the temperature of the cancer cells, thereby killing the cancer cells; or the nano-particles can be formed to encapsulate cancer-killing drugs, which are released into the cancer cell by the application of the magnetic field.

However, this process is in the early stages of development and has yet to reach a level of maturity where the physical processes and their limitations are well understood. Existing cancer treatment techniques using nano-particles fail to provide the necessary coordination among the characteristics of the nano-particles, concentration of nano-particles, duration of treatment, and applied fields to enable the generation of precisely crafted fields and their application in a mode and manner to be effective with a high degree of accuracy.

Thus, there presently is no procedure that can be used to accurately detect the presence of cancer cells in a living organism or treat the cancer cells, once detected, to destroy the cancer cells, without serious negative effects on the living organism. Present diagnostic and treatment procedures are macro and non-specific in their approach and are ineffective or can result in damage to the living organism in order to destroy the cancer cells.

BRIEF SUMMARY OF THE INVENTION

The above-described problems are solved and a technical advance achieved by the present System For Defining Energy Field Characteristics To Illuminate Nano-Particles Used To Treat Invasive Agents (termed "Invasive Agent Treatment System") which creates the pairing of energy fields with nano-particles to cause a thermal effect in the nano-particles, which thermal effect is transmitted into the biological cells of the invasive agent. The energy fields are derived from at least one or a combination of the following: an electric field, a magnetic field, an electromagnetic field (EM), an acoustic field, and an optical field. The Invasive Agent Treatment System provides the necessary coordination among the characteristics of the nano-particles, concentration of nano-particles, duration of treatment, and applied fields to enable the generation of precisely crafted fields and their application in a mode and manner to be effective with a high degree of accuracy. The energy field frequencies are in the hundreds of kilohertz or millions or billions of hertz, with energy field strengths ranging from a few hundred volts per meter to thousands of volts per meter, if an E-Field; alternatively, the magnetic fields (H-Field) are in the hundreds of kilohertz and higher with field strengths in the 10-20 thousand amps/meter. These energy field parameters are typical and nothing herein precludes other types of energy field parameters.

The nano-particles which are excited by these energy fields have characteristics which make them responsive to excitation typically by a given energy field type. Some nano-particles are responsive to only an E-Field; others are only responsive to an H-Field, while some are responsive to both. The induced effects in the nano-particle can be numerous; however, the predominant effect of interest is a thermal effect, where the exciting energy field causes the temperature of the particle, hence the surrounding biological material, to rise in temperature.

Two modes of cancer treatment are embodied herein: ablation and low temperature hyperthermia. In the ablation method, the nano-particles are illuminated by an energy field and the nano-particles thereby are heated to a temperature (for example greater than 42° C.) which causes the cells of the invasive agent to be heated to a temperature which kills the cancer cells over a given timeframe. The second method of cancer treatment uses Low Temperature Hyperthermia (LTH) to bring the nano-particles and the associated cancer cells to a temperature of 42.25° C. or cooler. This temperature causes the cancer cells, particularly cancer stem cells, to be stressed by a number of mechanisms which include: re-oxygenation, increased blood flow, change of acidity, and so on—environments that are harmful to cancer stem cells. By the application of the energy field to the nano-particles for a sufficient period of time, the heated cancer cells are destroyed with minimal production of Heat Shock Proteins, which enable cancer stem cells to survive normal killing temperatures.

This Invasive Agent Treatment System identifies nano-particle—energy field pairings which cause the optimal excitation of the nano-particles, based on a number of theoretical and analytical criteria, including the characteristics of the nano-particles, concentration of nano-particles, duration of treatment, and applied fields to enable the generation of precisely crafted energy fields and their application in a mode and manner to be effective with a high degree of accuracy where the net effect is a thermal rise in the nano-particles. In the case of ablation, the thermal rise is to a temperature which directly kills cancer cells. In the case of LTH, the objective is to stress and kill cancer stem cells, cells which are very resistant to heat ablation due to the production of Heat Shock Proteins, which protect the cancer cell from damage. LTH also kills in other ways, such as oxygenation—cancer stem cells prefer and live in a hypoxic environment; increasing the level of oxygen is one way to kill cancer stem cells that may have been already pre-stressed by a treatment of ionizing radiation or chemotherapy.

The description of the Invasive Agent Treatment System uses cancer as an example of an invasive agent, since much research has been done in this field and the diversity of cancers that are found in a living organism is extensive. Of note, while the methods and techniques described herein focus on breast cancer treatment, the technology is applicable to any type of cancer or other biological invasive agent, such as HIV or even the common cold. Since nano-particles are as small as the smallest of biological structures, these techniques are not limited to just cancer and treating cancer cells to a physical extent; but rather, the methods described herein could be used to treat virtually any type of invasive agent or non-normal biological material, behavior, mechanism, or process.

Note that the locus of the cancer cells may be dynamic, such as in the case of a blood-borne cancer. In this example, the movement of the cancer cells within the blood stream creates an added complexity to the treatment process. In cancers that are in the process of metastasizing, the blood system and the lymph system create pathways for the cancer to spread to other loci. Thus, there is a time domain component in conjunction with a spatial domain component for the treatment protocol. For most cancers, and breast cancer in particular, the time domain component can often be ignored and just the spatial domain component is of interest. However, even for breast cancer, depending on the type of energy field, the chest wall movement caused by breathing must be considered and extracted from the treatment process, if the illumination of the breast by the energy field is in a narrow range. In the case of breast cancer, placing the breasts between plates, as is done in present day mammograms, helps remove the breathing motion artifact. As discussed herein, treatment methods that use pulsed field excitation, where the pulses are relatively short in time, say one microsecond long, would help remove motion artifacts.

The target nano-particles are activated by a precisely crafted energy field to provide illumination of the target nano-particles with the minimum required energy to create the selected effects. Since there is a great diversity in cancer cells, there must be a corresponding diversity in the target nano-particles which are designed to be implanted in the specific cancer cells and be responsive to the applied energy fields. Furthermore, the site of the cancer can vary in terms of depth within the living organism; and this has significant implications in terms of the strength and focus of the energy fields, since each interface in the living organism encountered by the incident energy field(s) can cause dissipation, diffraction, and reflection of the incident energy field(s). Also, each living organism has characteristics that define the illumination environment and limitations on the type and duration of the energy fields that are used.

Certain energy field types, such as a magnetic field, are less susceptible to tissue interaction as the energy field propagates into the in vivo body to the nano-particle locus. However, if the magnetic field construct of field strength multiplied by the excitation frequency is too high, eddy currents can be induced in the tissue of the living organism, which can cause unintended heating. There is a balancing of illumination attributes that must be considered. While a magnetic field has less tissue artifacts to deal with, a magnetic field cannot be used when metallic objects are embedded in the living organism, such as pace makers, orthopedic screws/pins, and the like. An electric or electromagnetic field may be better suited for situations where metallic objects are present since it may be easier to highly target the illumination to just the area of interest versus a large macro region of the living organism.

Thus, the pairing of nano-particles to energy fields requires the consideration of a number of field illumination factors to include: energy field type, frequency, energy field strength, duration, energy field modulation, repetition frequency, beam size, and focal point. The determined energy field characteristics then are used to activate one or more energy field generators to generate an energy field having the selected energy field characteristics for application to the portion of the target living organism to treat the presence and locus of invasive agents in the living organism by the excitation of introduced nano-particles.

It is important to note that the activation of nano-particles is highly deterministic, meaning that a given nano-particle is optimally activated or excited by a given energy field of pre-defined characteristics. Generic or random energy field excitations do not optimally excite a given nano-particle. In fact, certain nano-particle types do not respond at all to certain energy fields, as is shown herein.

The following description provides a brief disclosure of these elements in sufficient detail to understand the teachings and benefits of the pairing energy fields with nano-particles. The description of the Invasive Agent Treatment System also teaches how to determine what type of energy field in which a nano-particle is optimally excited. It is expected that many other applications can be envisioned by one of ordinary skill in the art, and the methods described herein for field-particle pairing are simply one application of treatment methods, ablation and LTH, which is delimited by the appended claims.

BRIEF DESCRIPTION OF THE DRAWINGS

FIG. 2A is an example, in table format, of target particle characteristics for nano-particles;

FIG. 2B illustrates, in table format, the various nano-particle types as paired with energy field types;

FIG. 15 illustrates a graphical representation of the LTH nano-particle types, their energy field type, their energy field dependence, and temperature dependence;

DETAILED DESCRIPTION OF THE INVENTION

Figure 21:
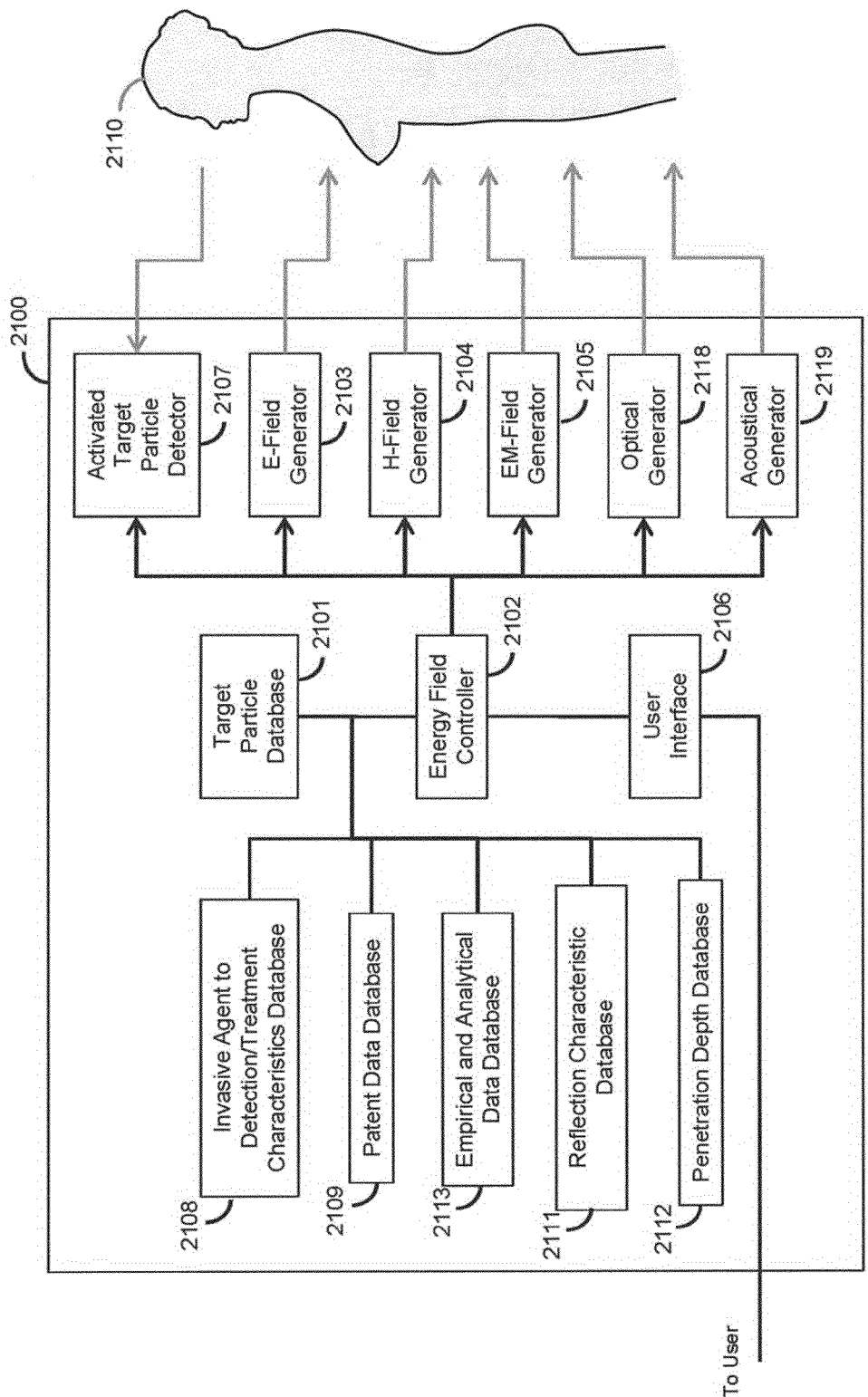
FIG. 21 illustrates, in block diagram form, the typical architecture of an Energy Field and Target Correlation System in which the present Invasive Agent Treatment System can be implemented.

FIG. 21 illustrates, in block diagram form, the typical architecture of Energy Field and Target Correlation System 2100 as used with a specific instance of a living organism 2110. In operation, the target portion of the living organism 2110 is populated with target particles of a predetermined type or types. This population of target particles could be delivered in a variety of fashions to include, but not limited to: intravenous delivery, injected delivery, a skin cream and the like. The target particles themselves can take on at least two generic forms of delivery after initial administration: active and passive. Active delivery particles are particles which are selectively taken up by the invasive agent or cancer cells because of a preferred antigen (or other substance), while passive particles use their shape, size, or physical configuration to be selectively taken up by the cancer cells. Alternatively, it is possible for all cell types, healthy and cancerous, to take up the target particles; and the cancer cells can cause the target particle to change, such as "melt" an outer layer off of the target particle because the pH of a cancer cell is typically different than the pH of a healthy cell. In this case, the two target particle types are now different: a modified target particle in the cancer cell and an original target particle in a healthy cell. Thus, in the healthy cell, where the shell did not melt or dissolve, the cytotoxin, for example, would not be released (but it would be released in the cancerous cell).

These target particles are designed to attach to or be absorbed by the cancer cells (invasive agents) of interest to enable treatment of the cancer cells. For the sake of simplicity of description, the target particles used herein as an illustration are nano-particles and these terms are used interchangeably, without intending to limit the scope of target particles that could be used. Some empirical evidence suggests that a higher uptake probability in cancer cells occurs if both IV and injection delivery are utilized simultaneously. The first is via Intravenous (IV) delivery of the target particle solution to the bloodstream. The second is via injecting the target particles directly at the tumor site. Nothing herein precludes any method of delivery of target particles to the cancer site; and all delivery methods, whether active or passive, are considered covered by this systems level approach to cancer treatment. Active delivery involves the use of targeting molecules or coatings on the exterior of the target particle that are preferred by cancer cells and rejected by other healthy cells. Passive delivery uses the unique physical attributes of the target particle, such as length or width, to only be taken up by cancer cells and not by other healthy cells. It is possible to use both Active and Passive methods in a concurrent fashion as well. Furthermore, healthy cells can uptake nano-particles, either the same as taken up by the cancer cells or other nano-particles specifically targeted to healthy cells.

After a sufficient preparation time to enable the target particles to reach their desired destination, the living organism 2110 is illuminated by energy fields which are automatically selected and produced by the Energy Field and Target Correlation System 2100 to enable the Activated Target Particle Detector 2107, which is responsive to activation of the target particles, for producing a human interpretable representation of the targeted portion of the living organism 2110 to illustrate the presence and locus of the activated target particles.

The Activated Target Particle Detector 2107 could take on a number of forms. The first form could be an ultra-sonic array that is designed to pick up or receive the emitted acoustical signature of the tissue and target particles when under a pulsed illumination, such as in thermal acoustic or photo acoustic imaging. The second form could be a microwave antenna receiving array that picks up the back scatter or scattering components of the tissue and target particles. These detectors, while not shown in FIG. 21, would reside at the input of Activated Target Particle Detector 2107.

In particular, there are a number of databases which maintain information which is relevant to the treatment process. In particular, a Target Particle Database 2101 maintains a listing of characteristics of at least one type of target particle from the characteristics of target particles including: size, shape, material composition, surface coating, geometry, and contents. The Invasive Agent-To-Detection Characteristics Database 2108 maintains data which characterizes the relationship between the invasive agent and the detection characteristics needed to produce a detectable effect for a selected type of target particle. In addition, Patient Data Database 2109 maintains patient-specific data which provides data regarding the age, sex, weight, prior surgeries, or other conditions relevant to the detection process. The Empirical And Analytical Data Database 2113 maintains information which has been collected via modeling, testing, theoretical computations, and the like. The Reflection Characteristics Database 2111 contains data which represents the percentage of an incident energy field which is reflected at the interface between two materials: biological, water, air, or the like. Finally, the Penetration Depth Database 2112 contains data which represents the attenuation of an incident energy field as it passes through a selected material. The number and contents of these databases are selected to illustrate the concepts of the Energy Field and Target Correlation System 2100 and are not intended to limit the application of the Energy Field and Target Correlation System 2100.

There are also one or more Field Generators 2103-2105, 2118, and 2119 for generating an energy field. An Electric Field Generator 2103 is shown for producing an electric field; a Magnetic Field Generator 2104 is shown for producing a magnetic field; an Electromagnetic Field Generator 2105 is shown for producing an electromagnetic field; an Optical Generator 2118 is shown for producing NIR, IR Optical, and UV inputs; and an Acoustical Generator 2119 is shown for generating sonic and ultrasonic inputs. Any combination of these Field Generators 2103-2105, 2118, and 2119 may be present and can be activated individually or simultaneously, as required. At the outputs of each of these field generators, 2103-2105, 2118, 2119, there are illumination radiators which may comprise antennas, antenna arrays, magnetic coils, and so on. The purpose of these radiators (not shown in FIG. 21 for clarity) is to provide the energy field or the energy impulse that excites the tissue and the target particles. The radiators could be linearly polarized, such as in horizontal and/or vertical; or they could be elliptically polarized; or they could be circularly polarized such as in Left Hand or Right Hand Circular. The output energy field might consist of continuous, modulated, or pulsed energy in any frequency band from acoustic through RF and microwave through infrared and optical.

An Energy Field Controller 2102, which is responsive to a user selecting, via the User Interface 2106, at least one type of the target particles and identifying a portion of a target living organism which contains these target particles, automatically selects energy field characteristics from the characteristics of energy fields including: field type, frequency, field strength, duration, field modulation, repetition frequency, beam size, and focal point, to energize the selected target particles in a selected manner in the identified portion of the target living organism. Thus, the user inputs data relating to the class of target particles and the portion of the living organism that is being analyzed, which causes the Energy Field Controller 2102 to automatically determine the appropriate set of energy field characteristics which are required for application to the designated portion of the target living organism to activate the target particles to respond in a detectable manner to enable the identification, via an Activated Target Particle Detector 2107, of a presence and locus of invasive agents in the living organism (as disclosed in further detail below). The Energy Field Controller 2102 uses the automatically determined set of energy field characteristics to activate the corresponding Energy Field Generator(s) 2103-2105, 2118, and 2119 to output the corresponding energy fields as defined by the set of energy field characteristics. It should be noted that an automated system would help improve accuracy and prevent human imaging errors; but nothing herein prevents this system from being operated in a manual form, should a special case arise wherein a manually-entered algorithm could potentially enable higher imaging contrast or resolution; or better, a more efficacious treatment protocol.

Energy Field Controller

The Energy Field Controller 2102 executes a process which automatically selects energy field characteristics from the characteristics of energy fields including, but not limited to: field type, frequency, field strength, field modulation, repetition frequency, beam size, and focal point, to energize the implanted target particle in a selected manner in a portion of the target living organism. The present Invasive Agent Treatment System comprises this process as illustrated in steps 2206-2214 of FIG. 22A and also comprises the Target Particle Database 2101, Invasive Agent-To-Detection Characteristics Database 2108, Patient Data Database 2109, Empirical And Analytical Data Database 2113, Reflection Characteristics Database 2111, and the Penetration Depth Database 2112, along with the data illustrated in FIGS. 10-19 herein.

Figure 22A:
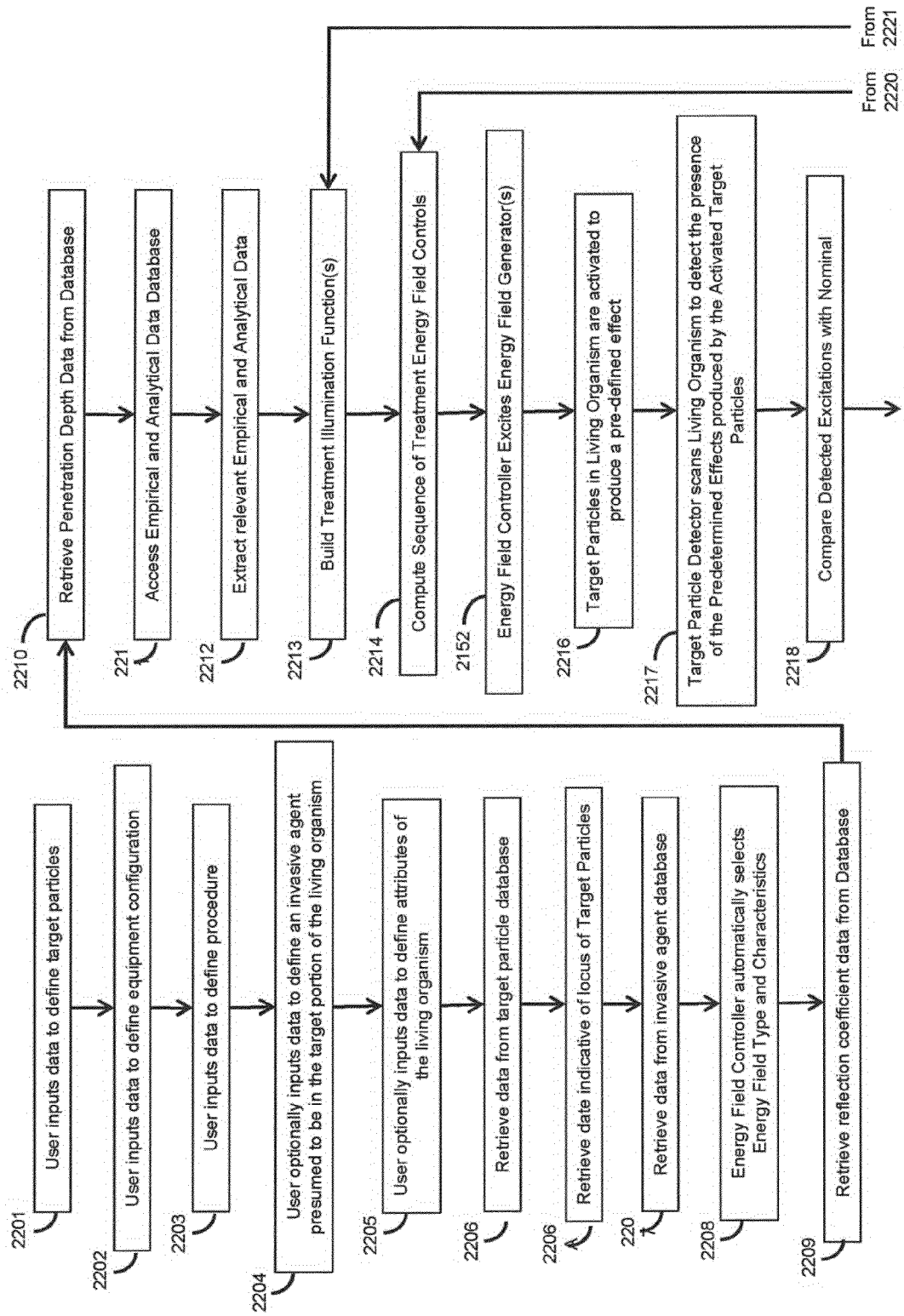
FIGS. 22A and 22B illustrate, in flow diagram form, the operation of the Energy Field and Target Correlation System to image and treat invasive agents in a target portion of a living organism.
Figure 22B:
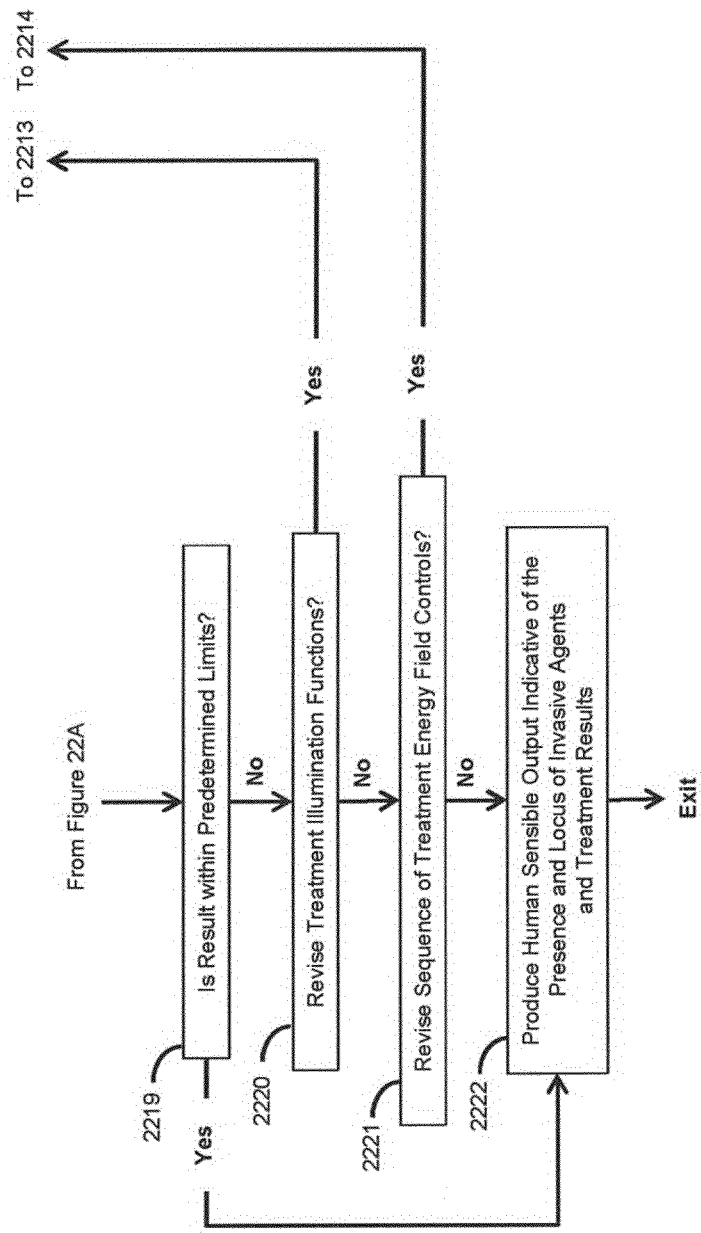

There are a number of logical feedback loops, where the feedback enables the system to have an optimum response. This feedback largely takes place between the Activated Target Particle Detector 2107 and the Energy Field Controller 2102. FIGS. 22A and 22B show numerous feedback, as well as feed-forward, loops.

FIGS. 22A and 22B illustrate in flow diagram form the operation of the Energy Field and Target Correlation System 2100 to treat invasive agents in a target portion of a living organism. The Energy Field and Target Correlation System 2100 receives a set of user-provided input data to define the protocol and equipment configuration in the living organism, as well as the target particles that have been deployed in the living organism. This data then is used by the Energy Field and Target Correlation System 2100 to automatically build a set of illumination functions and compute the sequence of energy field controls that are required for the invasive agent detection and treatment protocols. In addition, the Energy Field and Target Correlation System 2100 makes use of dynamic feedback to adjust the energy fields during the execution of a selected protocol.

At step 2201, the user inputs data via User Interface 2106 to the Energy Field and Target Correlation System 2100 to define target particles deployed in the living organism 2110, such as in the breast of the woman 2110. At step 2202, the user optionally inputs data via User Interface 2106 to the Energy Field and Target Correlation System 2100 to define the configuration of the equipment, such as the two table configurations shown in FIGS. 8 and 9. If the equipment configuration is invariant, this step can be skipped. The user also can input data via User Interface 2106 to the Energy Field and Target Correlation System 2100 to define the procedure being executed. The user then can input data into the Energy Field and Target Correlation System 2100 at step 2204 via User Interface 2106 to define an invasive agent (such as breast cancer) presumed to be in the target portion of the living organism 2110. At step 2205, the user optionally inputs data via User Interface 2106 to the Energy Field and Target Correlation System 2100 that identifies a selected living organism 2110 and the attributes of this living organism 2110. This pairing of input information defines the particular application that must be addressed by the Energy Field Controller 2102 in automatically generating an illumination protocol that is effective for this application, yet not excessive and potentially damaging to the living organism 2110.

In response to these data inputs, at step 2206, the Energy Field Controller 2102 retrieves data from the Target Particle Database 2101; and, at step 2207, the Energy Field Controller 2102 retrieves data from the Invasive Agent Database 2108. This retrieved data, in conjunction with the user input data, is used by the Energy Field Controller 2102 at step 2208 to automatically select energy field characteristics; this also could be set manually, depending on specific circumstances. The energy field characteristics include: field type, frequency, field strength, field modulation, repetition frequency, beam size, focal point, and the like. These energy field characteristics are needed to produce a precisely crafted energy field with is mapped to the target particle characteristics and the target portion of the living organism 2110.

At step 2209, the Energy Field Controller 2102 retrieves reflection coefficient data from the Reflection Characteristic Database 2111 and also retrieves penetration depth data at step 2210 from the Penetration Depth Database 2112 (this is for an E-Field component; the H-Field excitation is less susceptible to these issues as previously discussed herein). This data enables the Energy Field Controller 2102 to account for the particular tissues that the generated energy fields will traverse to reach the deployed target particles. This information is used to adjust the selected energy field characteristics as computed at step 2208.

At step 2211, the Energy Field Controller 2102 accesses the Empirical And Analytical Data Database 2113 that maintains information which has been collected via modeling, testing, theoretical computations, and the like. This data represents the experiential knowledge that can be used by the Energy Field and Target Correlation System 2100 to automatically set the illumination functions and energy field generator controls. Thus, at step 2212, the Energy Field Controller 2102 extracts whatever data is relevant to the proposed protocol from the Empirical And Analytical Data Database 2113. This step completes the data input, collection, and extraction functions.

At step 2213, the Energy Field Controller 2102 proceeds to automatically build a set of treatment illumination functions which are used to detect the presence and locus of the invasive agents in the living organism. These illumination functions are then used by the Energy Field Controller 2102 to compute a sequence of treatment energy field controls, which are the control signals used to activate selected Energy Field Generators 2103-2105, 2118, and 2119 to produce the illumination energy fields necessary to activate the target particles to produce a desired and detectable effect via the application of the treatment energy field controls at step 2215.

The energy field generator(s) produce one or more energy fields corresponding to the selected energy field characteristics to illuminate the target portion of the living organism 2110. At step 2216, the target particles in the living organism are activated to produce a predetermined effect which can be detected at step 2217 by the Activated Target Particle Detector 2107 and which enable differentiation between the activated target particles in their associated invasive agents and the surrounding normal cells in the living organism. Then at step 2218, the Activated Target Particle Detector 2107 compares the detected excitations with what is expected and, at step 2219, determines whether the detected effects are within predetermined limits. As an example, if the image shows the entire breast as being cancerous, there is likely an error somewhere that needs to be resolved. If so, the Activated Target Particle Detector 2107 produces a human sensible output at step 2222 indicative of the presence and locus of invasive agents as signified by the predetermined effects produced by the activated target particles. If not, processing advances to step 2220 where a determination is made whether the illumination functions need to be adjusted by routing back to step 2213. If not, processing advances to step 2221 where a determination is made whether the treatment energy field controls need to be adjusted by routing back to step 2214. If not, processing advances to step 2222. The process then terminates after step 2222. An image of the invasive agent, and the treatment results, is realized at step 2222. This image can be used by doctors and treatment teams to understand the spatial extent of cancer and propose likely further treatment methods for the imaged cancer.

Invasive Agent Pairing with Target Nano-Particles

Each target nano-particle to living organism to invasive agent sequence is unique, to some degree, and this is part of the system's process implemented by the Invasive Agent Treatment System, as executing in Energy Field Controller 102, to recognize and adapt for this uniqueness or variability to create a custom or semi-custom illumination regimen or protocol. While certain nano-particles behave differently under illumination, a number of theoretical characteristics, verified by empirical data, describe parameters that can be controlled in the energy field domain to induce certain thermal behaviors in the nano-particle domain. The two generic thermal realms are Ablation and Low Temperature Hyperthermia (LTH).

Figure 1A:
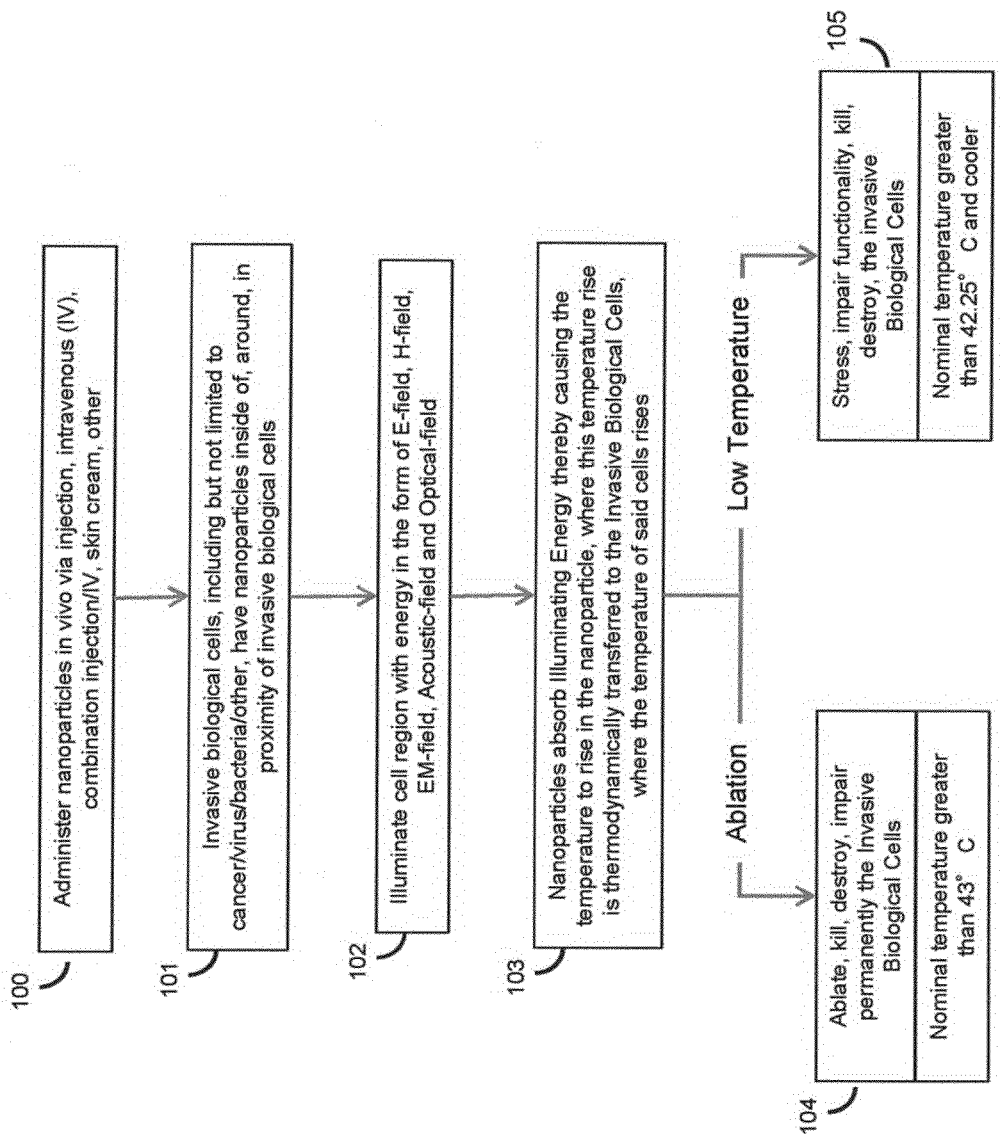
FIG. 1A illustrates, in flow chart form, the typical treatment steps used in both ablation or LTH treatment protocols.

In FIG. 1A, the process steps of Ablation and LTH are described. At step 100, the nano-particles are administered in vivo (in the body) via intravenous (IV) means, by direct injection means, by a combination, or by other means to include a skin cream.

These target particles are designed to attach to or be absorbed by the cancer cells (invasive agents) of interest to enable the destruction of the cancer cells. For the sake of simplicity of description, the target particles used herein as an illustration are nano-particles, and these terms are used interchangeably without intending to limit the scope of target particles that could be used. Some empirical evidence suggests that a higher uptake probability in cancer cells occurs if both IV and injection delivery are utilized simultaneously. The first is via IntraVenous (IV) delivery of the target particle solution to the bloodstream. Some research is showing as much as 8% to 10% of the delivered particle count is getting to and residing in cancer cells. The second is via injecting the target particles directly at the tumor site. Nothing herein precludes any method of delivery of target particles to the cancer site; and all delivery methods, whether active or passive, are considered covered by this approach to cancer treatment. Active delivery involves the use of targeting molecules or coatings on the exterior of the target particle that are preferred by cancer cells and rejected by other healthy cells.

Passive delivery uses the unique physical attributes of the target particle, such as length or width, to only be taken up by cancer cells and not by other healthy cells. It is possible to use both active and passive methods in a concurrent fashion as well.

At step 101, there are a number of possible invasive agents identified that can be found in a living organism; and these can include viruses, bacterial, cancers, and the like. An infection is the detrimental colonization of a host organism by a foreign parasite species. Infecting organisms seek to utilize the host's resources to multiply, usually at the expense of the host. The immune system of mammalian hosts reacts to infections with an innate response, often involving inflammation, followed by an adaptive response. Colloquially, a pathogen is usually considered a microscopic organism though the definition is broader, including macro parasites, fungi, viruses, prions, bacteria, and viroids. A further class of invasive agents is cancers, which is a class of diseases in which a cell or a group of cells display uncontrolled growth, invasion (intrusion on and destruction of adjacent tissues), and sometimes metastasis. A separate class of agents is not strictly "invasive" in nature, such as fat cells, uric acid "crystals", kidney stones, etc., but is included in the classification of invasive agents herein for simplicity of description. Cancer (medical term: malignant neoplasm) is a class of diseases in which a cell, or a group of cells, display uncontrolled growth, invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor but some, like leukemia, do not.

At step 101 in FIG. 1A, the nano-particles are now residing in the cancer cells. At step 102, the cancer cell region now holding nano-particles is illuminated with an energy field in a predetermined fashion: E-Field, H-Field, EM-Field, and so on. At step 103, the nano-particles absorb energy from the illuminating field and the result is a rise in temperature of the nano-particles themselves, which in turn causes a rise in temperature of the cancer cells in which they are residing or in the proximity.

Figure 10:
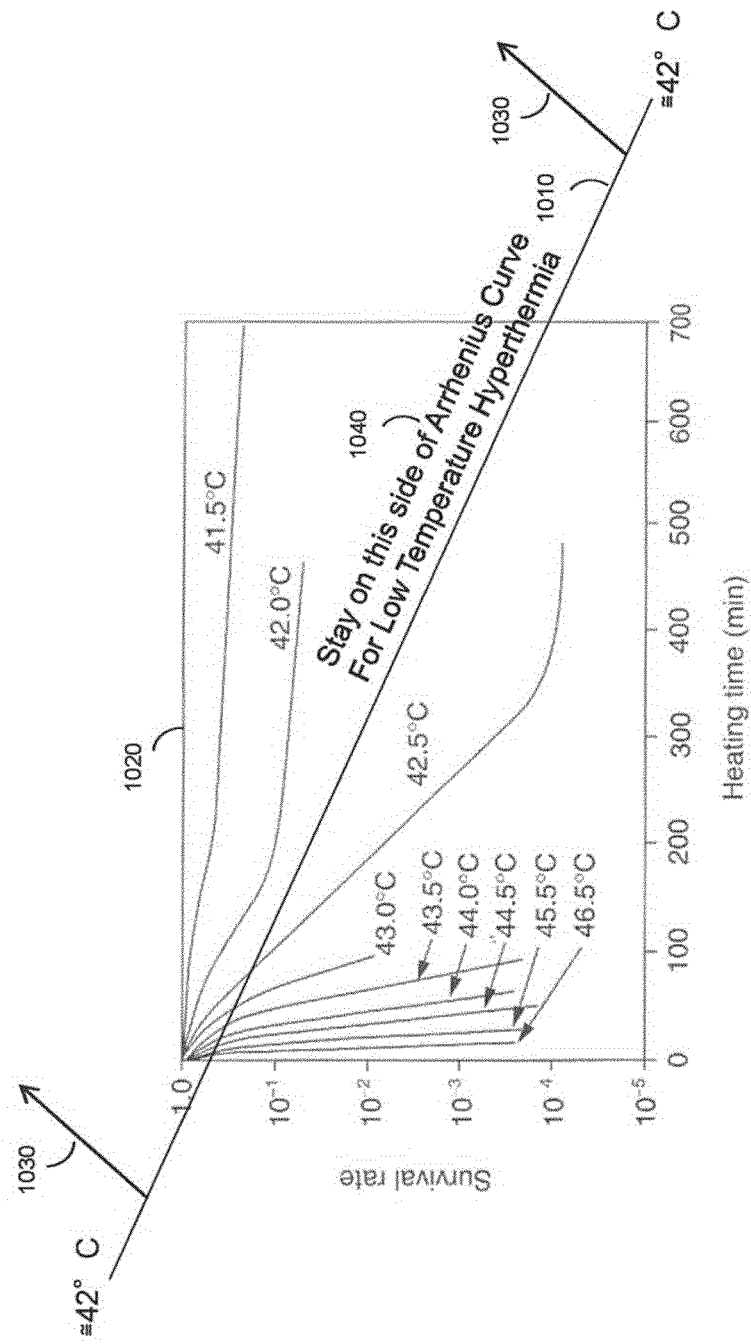
FIG. 10 illustrates a graphical representation of the Arrenhius curve of cellular death over time versus temperature.

At step 104, thermal ablation occurs where the temperature of the cancer cells exceeds 43° C. and, over time, the cancer cells are killed. FIG. 10 shows the cell death rate versus temperature versus time. Above 43° C., the cancer cell death rate versus time becomes very steep, meaning that the cancer cells are dying rapidly. Note that the temperature rise from an ambient human body of 37° C. to a cancer cell killing temperature of at least 43° C. is only 6° C. of temperature rise. The cancer cell death region is the left of line 1010 and describes the region opposite of the direction of arrows 1030.

In contrast, at step 105, the LTH method is realized. Here the desired temperature of the cancer cells is 42.25° C. and cooler. Note that the exact temperature can be person dependent, so adjustment may be necessary to optimize the LTH process for any given person. This is the region in FIG. 10 as indicated by arrows 1030 to the right of line 1010 as described by 1040. In this region, a number of positive biological things happen to maximize the probability that heat resistant cells, such as cancer stem cells, are killed. Things like re-oxygenation and minimization of Heat Shock Proteins are key attributes of the LTH process.

Figure 1B:
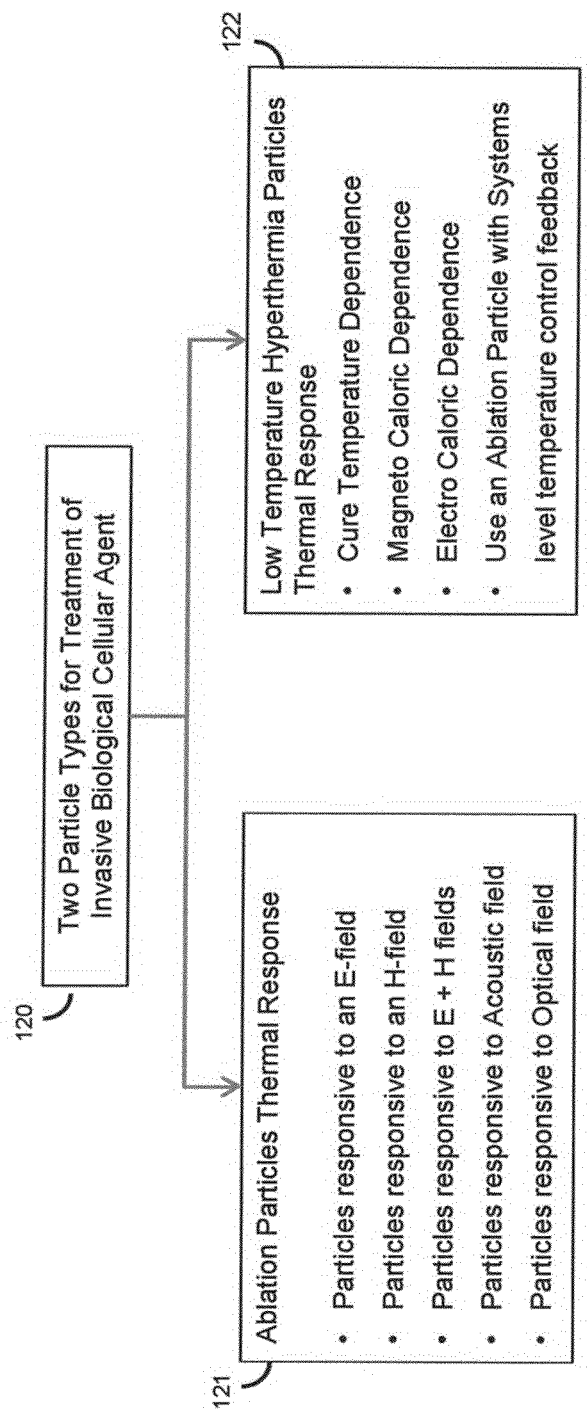
FIG. 1B illustrates the types of nano-particles paired with a responsive energy field type for ablation or LTH treatment protocols.

FIG. 1B shows the corresponding nano-particles for the two thermal treatment modalities: Ablation and LTH. For ablation, there are five generic nano-particle types that are thermally responsive to a given energy field type: E, H, EM, acoustic, and optical fields. For LTH, three nano-particles and one method realize the creation of an LTH environment: a Curie nano-particle, a magneto-caloric nano-particle, and an electro-caloric nano-particle. The systems method uses a feedback approach to modify the excitation function to realize a target temperature using a nano-particle that might have nominally come from the ablation family of nano-particles.

FIG. 2A is a target particle database that describes nano-particles conducive to the ablation process. These nano-particles are made of various materials and are responsive to energy field types as described. FIG. 2B is again for nano-particles in the ablation method being used, for example, in breast and lung cancer. The nano-particles for the LTH methods are described later herein.

Particles in Electric Fields

For virtually all metals, an H-Field excitation produces stronger heating. However, in those compounds that have an odd number of oxygen atoms, the heating is faster with the E-Field. This is because a single oxygen atom or odd numbers of oxygen atoms are dipolar in nature, and heat faster in an E-Field (vs. an H-Field). A dipolar substance is highly susceptible to heating in an electric field; the molecule of water for example, $H_2O$, having a single oxygen, due to uneven sharing of electrons in time in the $H_2O$ structure, creates a polar spatial extent that is physically rotated as the electrical phase of the E- or EM-Field passes over or through the substance. This is how standard microwave ovens work, in particular exciting water molecules where the rotation of said water molecules causes inter-molecule friction and thereby heat.

Figure 3:
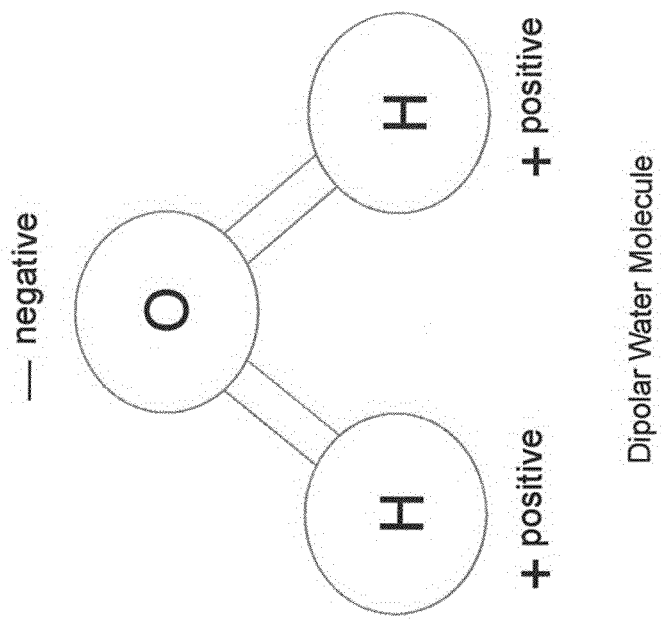
FIG. 3 is a diagram of a water molecule, showing its dipolar nature.
Figure 4:
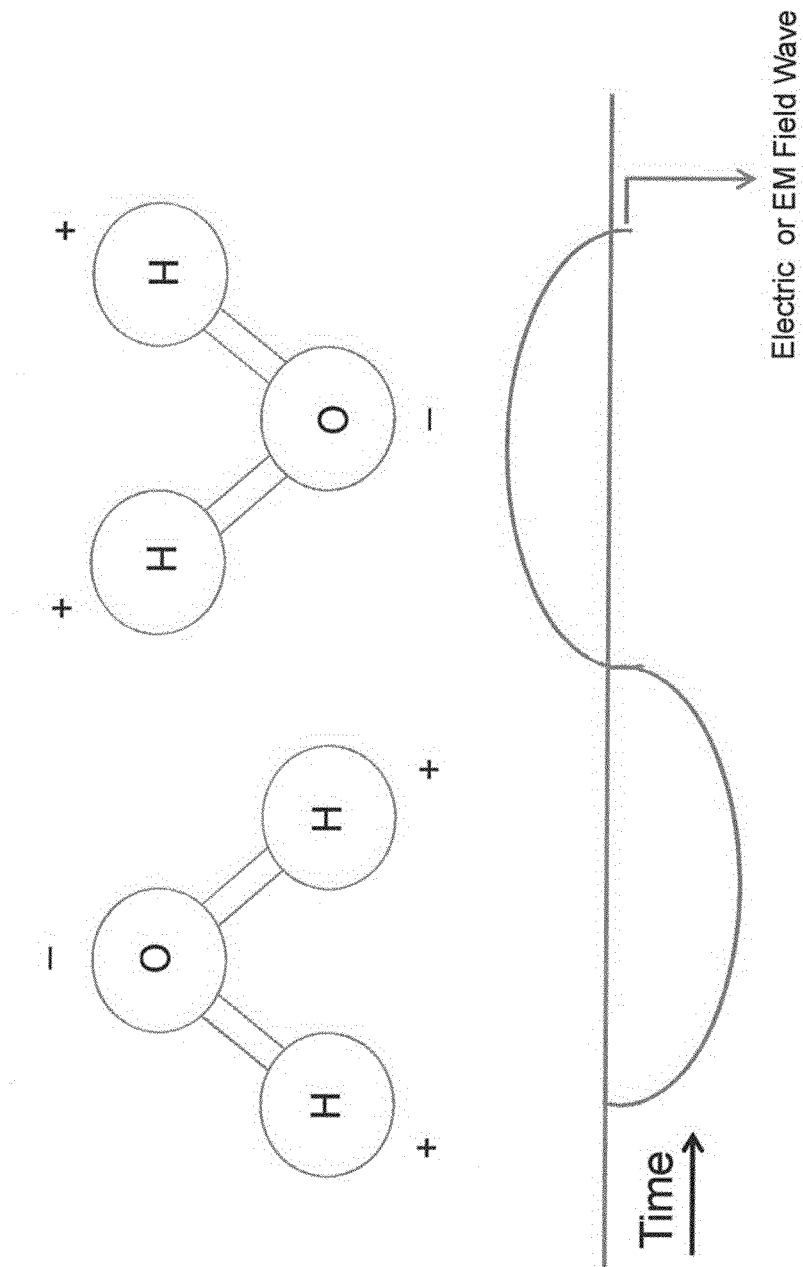
FIG. 4 is diagram of a water molecule in an electric or EM-Field.

In FIG. 3, a water molecule is shown with its corresponding dipolar charges. It is this non-uniform sharing of electrons when the atoms form the molecule where, in time, the non-uniform electron sharing causes a dipolar charge. When this dipolar charge is placed in an electric field, as shown in FIG. 4, it causes the water molecule to rotate with the phase of the applied energy field. This rotation or partial rotation (frequency dependent) causes molecular friction which causes heat.

Figure 11:
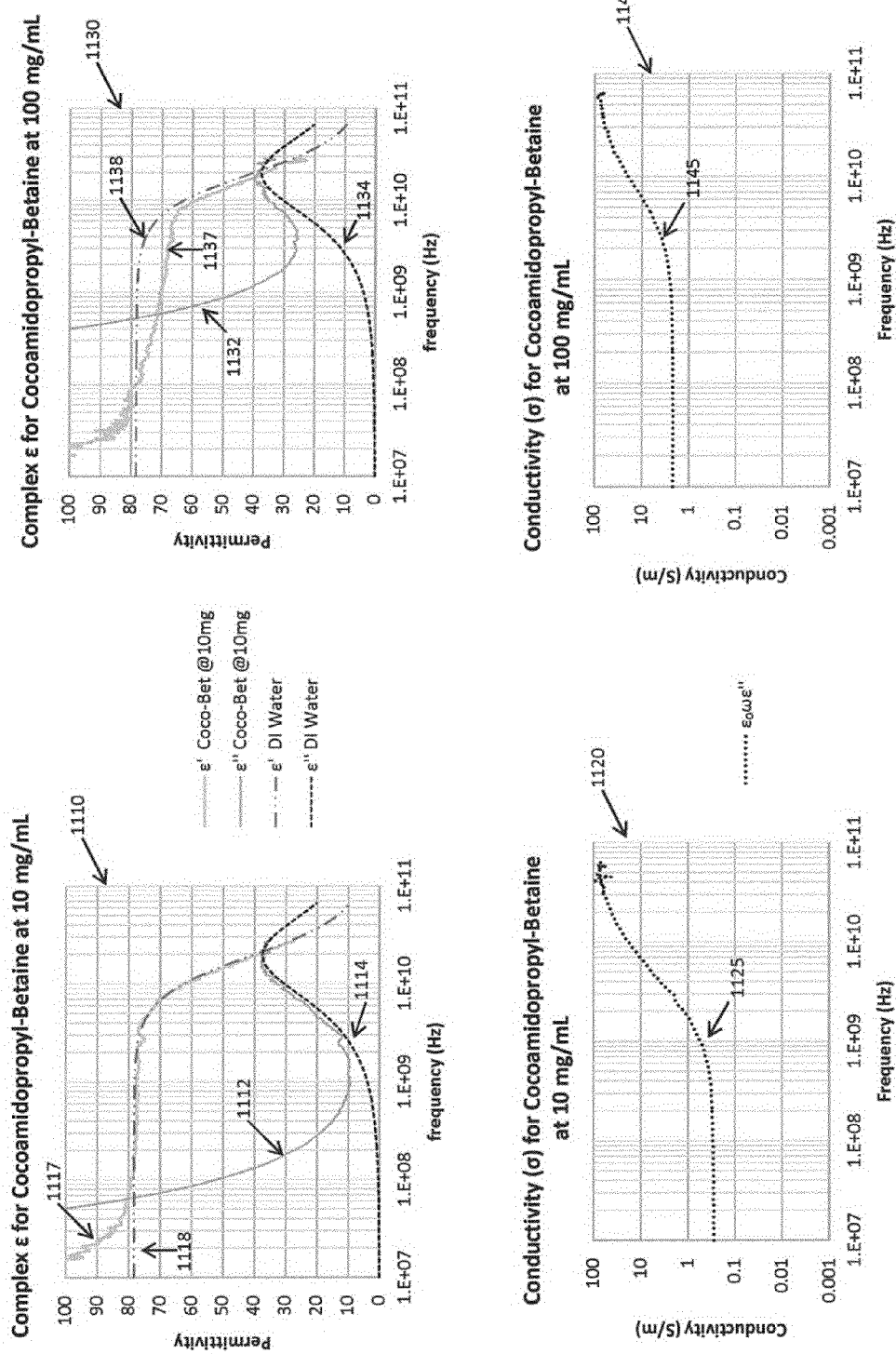
FIG. 11 illustrates the measured real and imaginary parts of the permittivity response of a surfactant versus frequency at different surfactant concentrations.

The Debeye response defines how a polar molecule behaves in the presence of an electric field of a given frequency. It is the imaginary part of the complex permittivity which defines the relative ability of a substance to heat faster than its water counter part. In FIG. 11 in graph 1140, the imaginary part of the permittivity of water is plotted. Note that if the excitation E-Field frequency (or EM-Field) is below 300 MHz, there is virtually no heating of water. In the lower 20 GHz range, the heating of water is maximized. While this is discussed in greater detail later in this specification, what is desired are materials that exhibit a significant delta over water in their imaginary part of their permittivity. In this way, the nano-particles heat faster than the water of the tissue of the living organism, thereby not harming the tissue while causing the nano-particles to heat and kill cancer cells. For example, if the excitation frequency were below 300 MHz, virtually no water heating occurs, meaning tissue does not heat up. So nano-particles that are responsive at 3000 MHz and below in an electric field are not competing with the tissue also being heated.

Figure 5:
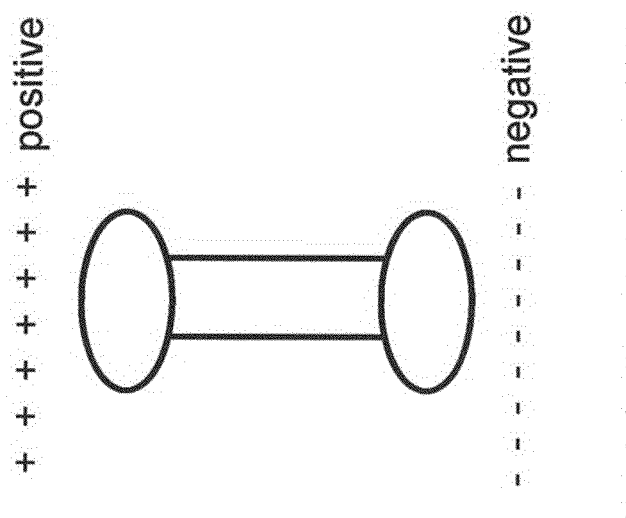
FIG. 5 is diagram of a dumbbell shaped nano-particle having dipolar attributes.
Figure 6:
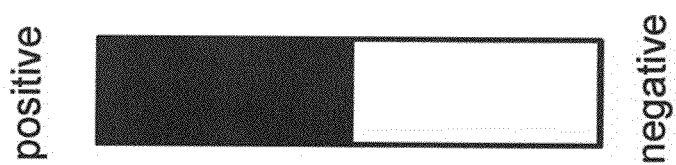
FIG. 6 illustrates a diagram of a generic dipolar particle.
Figure 7:
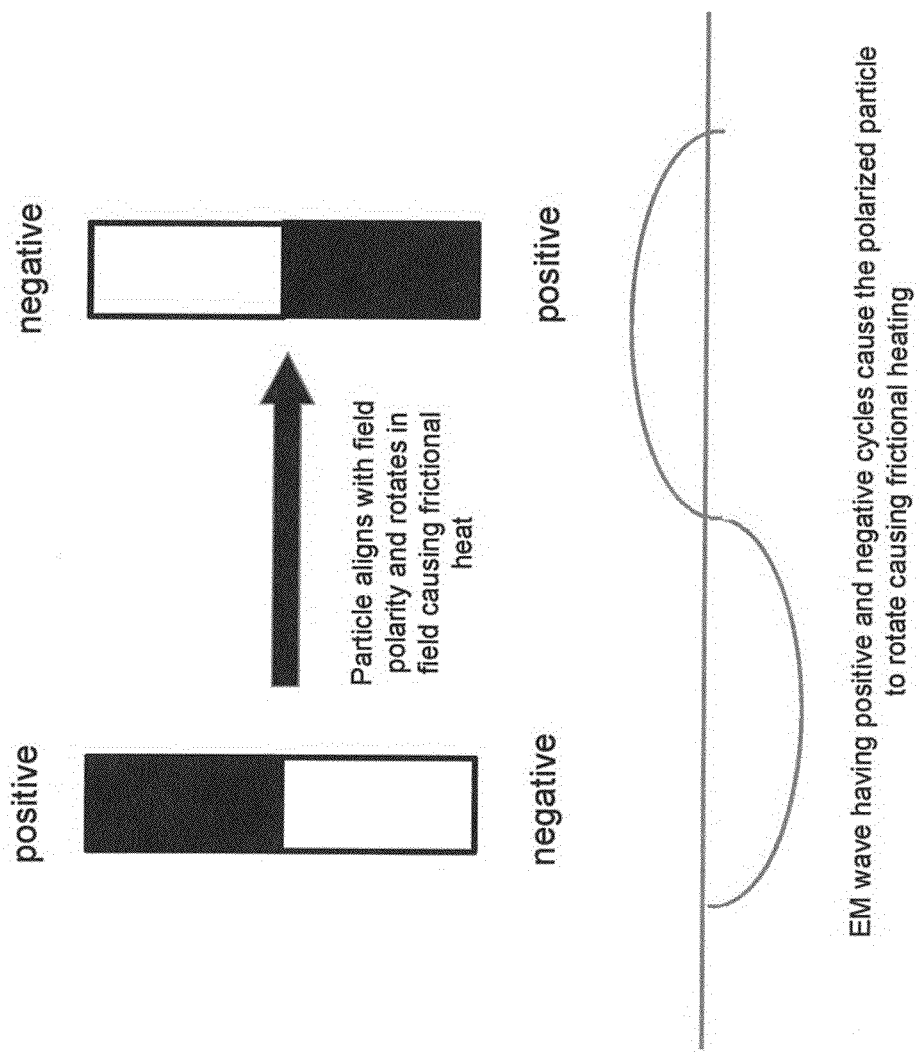
FIG. 7 illustrates a diagram of a generic dipolar particle in an electric or EM-Field.

In FIG. 5, a generic nano-particle shape is envisioned which has a polar charge as well as rotatable mass. This type of nano-particle configuration heats faster than other types of nano-particles when in an electric field or an EM-Field. Alternatively, an example nano-particle is shown in FIG. 6 where the entire half of the particle is polar. FIG. 7 shows how this type of nano-particle behaves in an illuminating electric field or an EM-Field wave. Since a nano-particle has greater mass than a water molecule, for example, a rotating nano-particle causes greater thermal creation than a rotating water molecule.

Note also that the heating mechanism can also be caused by eddy currents in the nano-particle, even if the nano-particle does not physically rotate. This generally is true for metallic nano-particles but could also be embodied in other material types such as dielectrics.

Figure 8:
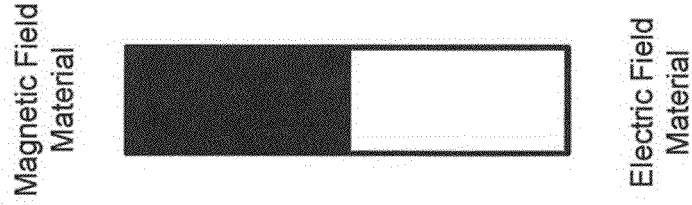
FIG. 8 depicts a diagram of a particle that has both magnetic and electric responsive material types.
Figure 9:
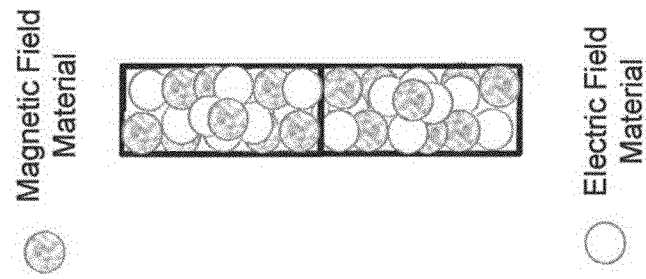
FIG. 9 illustrates a diagram of a nano-particle that has a uniform distribution of both magnetic and electric field responsive materials.

FIG. 8 contemplates a nano-particle which is made of material types responsive to both magnetic and electric fields. This nano-particle is illuminated by a magnetic field which causes heating in the half of the nano-particle susceptible to a magnetic field; similarly the electric field causes heating in the half of the nano-particle susceptible to an electric field. An EM-Field, since it contains both energy field types, naturally heats the combination nano-particle. FIG. 9 is a more uniform distribution of the material types which are inductive to heating by a given energy field type.

In particular, both PEG (PolyEthyleneGycol) nanospheres and iron ferrite ($Fe_3O_4$) nano-rods have been shown to greatly enhance tissue heating upon the application of quasi steady state energy (after tens to hundreds of seconds)—PEG being susceptible to an electric field while iron ferrite being susceptible to a magnetic field. An iron ferrite sphere coated with PEG would ostensibly be susceptible to both E- and H-Fields, as well as an EM-Field. The size, shape, and material composition of nano-particles (target particles) that lead to maximum heating at RF frequencies have not been investigated in the literature. These relationships are described in detail herein.

Target Particle Heating

Materials that have bound electrons preferably are heated using an electric field, and this is also the case for dielectrics which have bound electrons. Materials with free electrons generally are heated better in a magnetic field. In addition, materials that have an odd number of oxygen atoms always heat better in an electric field. This is because of the manner in which the electrons are shared in the orbital of the molecule describing the material, thereby making the molecule dipolar in its charge, further making it susceptible to physical rotation in an electric field as the phase of the wave changes as it passes over and through the molecule. This creates molecular motion, hence friction, hence heat. Thus, materials having a single oxygen atom, three oxygen atoms, five oxygen atoms, and so on are better heated in an electric field, while materials with an even number of oxygen atoms are better heated in a magnetic field.

To heat a target particle with electric or electromagnetic energy, it is clear that the particle must have some non-zero value of the imaginary part of the permittivity (and perhaps conductivity, in some situations). Effective heating means that in the material permittivity $\in = \in' - j\in'' = (\in_r - j\sigma/\omega\in_0)\in_0$, all loss mechanisms are described by finite, non-zero $\in''$, associated with $\sigma$, regardless of the nature of the loss (conduction, dipolar friction, etc.). Thus, the imaginary part of the effective permittivity must be non-zero at the frequency of illumination.

In general, any material may be heated by electric or electromagnetic energy, but the degree to which that happens is dependent on:

Frequency of the electromagnetic energy,
Intensity of the electromagnetic energy,
Proximity to the source of the electromagnetic energy,
Conducting or non-conducting nature of the material,
Nature of the material: how glossy, complex permittivity (real and imaginary), complex permeability (real and imaginary).

The induced power (power dissipated), or heating, in a particle is:

A multiplier of angular excitation frequency, where it is dependent on the angular frequency and the value of the imaginary part of the permittivity at the given angular frequency;

A function of field strength squared (E or H);

Particle size dependent: the selection of using E or H is also particle-size dependent (for a larger gold particle, 10 nm vs. 5 nm, the 10 nm particle favors H-Field excitation as the key imaginary part of the "polarization" is higher by a factor of about 10×;

Some particles of smaller sizes will not heat in an electric field, while larger sized particles will substantially heat;

A function of particle radius cubed for E-Fields, and radius to the fifth power for H-Fields (for metallic spheres);

Is a linear multiplier of $\in_0$ for E-Fields;

Is a linear multiplier of $\mu_0$ for H-Fields; and

Does not depend on skin depth in the nanoparticle sized realm.

The magnetic heating is also a function of complex magnetic dipoles and the excitation and realization of those dipoles in the material itself. Even a non-magnetic metallic sphere in a magnetic field has eddy currents induced which cause heating.

Electric Field Heating

The relative static permittivity of a solvent is a good measure of its polarity, and the dielectric constant, hence polarity, is temperature dependent. This means that, as a material heats up, its relative $\in_r$ changes, as does its polarity, further meaning that the illumination function needs to change to maintain a constant rate of heating. Thus, the excitation field is not static and changes during the process of heating, based partially on the change in polarity and $\in_r$. This could be as simple as a lookup table mapping tissue temperature to illuminated power, or it could involve active temperature feedback where the temperature is measured and that temperature is reported to the system controller which then adjusts its illumination power level accordingly.

Nano-particles that exhibit, either naturally or via a coating, a polarity in the spatial domain get hot via the "dipolar heating" effect in an E-Field. In addition, if the nano-particles were, over time, to become less dipolar as the temperature rose, the maximum defined temperature would be reached naturally and any further excitation would not cause an increase in temperature. This would be a natural limiting function, offering an added degree of heating safety.

For a treatment protocol, the heating of the nano-particles in the cancer cells must exceed the heating of healthy tissue in the vicinity of the location of the nano-particles. For an imaging protocol, the heating of the nano-particles in the cancer cells just needs to be different than neighboring healthy tissue. If the frequency of the applied energy field is low, the E-Field component of the applied energy field provides a low level of heating of the surrounding healthy tissue; and the tissue heating increases when the frequency of the applied energy field is raised to higher levels. Thus, one method to develop a temperature differential between nano-particles and healthy tissue is to use a lower RF frequency.

By examining the well-known equations which define the illumination function for both E- and H-Fields, the key drivers can be identified to maximize the particle-illumination mapping function; that is, which illumination functions are optimal for maximum heating of a given target particle material type. Equations 1 and 2, below, define the power dissipated in a metallic target particle that is contained in an electric field. Equation 1 defines the electric field heating of a nano-particle in watts. As previously mentioned, the absorbed power is a function of the E-Field squared (actually, this is the complex E-Field). The power is a linear function of the excitation frequency, in this case ω or angular frequency, including the imaginary part of the permittivity at the given excitation frequency.

Thus, in an electric field, the objective is to find target particle material types which heat faster than the surrounding healthy tissue. In this manner, cancerous tissue containing target particles (such as nano-particles) is heated without harming healthy tissue.

$$P_{abs}^E(\omega) = \omega 2\text{Im}(\alpha_E) \quad \varepsilon_o \frac{<|\vec{E}|^2>}{2} \quad (1)$$

The relative permittivity of the target particle being illuminated, as shown in Equation 2, which dovetails into Equation 1 as $\alpha_E$, provides insight into the behavior of material with differing dielectric constants. As an example, in an electric field, the heating of the target particles must exceed the heating of tissue in the vicinity of the location of the target particle. The heating of tissue is dispersive with the illumination frequency; as the frequency changes, the relative conductivity and permittivity of tissue changes. Different tissue types also have different permittivity and conductivity, again changing with frequency. Cancer also has its own unique dispersive electrical properties.

$$\alpha_E = 4\pi R^3 \frac{\varepsilon_r - 1}{\varepsilon_r + 2} \quad (2)$$

In Equation 2, the relative permittivity is a complex value, having both real and imaginary values. It is the imaginary portion of the complex permittivity that determines the loss a given material has in an electric field. Another defining factor is the loss tangent, which is a function of the ratio of the imaginary part to the real part of the relative permittivity; again, a dispersive complex value always changing with frequency. For Equation 2, the relative dielectric constant of a conductor in general has a real value that is negative and an imaginary value that is very large. For example, silver's complex dielectric constant is $-85+j8*10^{12}$. Note that the real part is negative and the imaginary part is rather large. The magnitude of $\varepsilon_r$ is >>greater than 1, as is the case for metals, meaning Equation 2 does not permit heating of a conductive metal such as silver. In this case, a magnetic field is the preferred field for materials with properties like silver.

If the excitation frequency goes from 13.56 MHz (a common frequency band allocated by the FCC for medical devices) to 3 GHz, the power absorbed by the target particle goes up by a factor of 221 times, a linear relationship, provided that the imaginary part of the permittivity does not change with frequency. This means that, all other variables being equal, illuminating a target particle at 3 GHz has 221 times the power absorbed if the illumination were at 13.56 MHz. This is important. It means that the electric field strength at 3 GHz can be almost 15 times less strong than the electric field at 13.56 MHz to obtain the same results. This is because of the squared relationship of the field strength. Thus, illuminating at a higher frequency offers a safety factor in terms of illumination energy field strength, where human tissue is involved, to offer significantly lower illumination levels. Thus, higher frequencies realize the same power absorbed at the target particle level as lower frequencies, but with much lower electric field strengths. Similar relationships exist for magnetic field excitation of nano-particles.

Tissue has three major frequency vs. permittivity dispersive regions: alpha—beta—gamma, all of which are frequency dependent. Alpha dispersion is at low frequencies and has very little engineering impact. Beta dispersion occurs at frequencies from around 1 KHz to the GHz region, and gamma dispersion begins around 10 GHz. This behavior affects the complex permittivity which affects its heating rate in an electric field. Without going into a lot of detail regarding tissue heating, it is sufficient to say that the target particle heating rate must exceed the tissue heating rate when the illumination function is an electric field. To be clear, the heating by-product of tissue, with or without nano-particles, in an electric field is not governed by Equations 1 and 2. It is governed by other equations and the general Specific Absorption Rate (SAR) equation, shown as Equation 3 below. Equations 1, 2, 4, and 5 are for heating of particles. Thus, tissue containing particles would have two sets of equations governing the overall heating: one set for the particles and the second set for the tissue alone.

The Specific Absorption Rate is governed by the following Equation 3, which describes the heating of tissue in general. For this to work, Particle Absorption with associated thermodynamic heat transfer to the cancer cell must be greater than the SAR for the surrounding healthy tissue; and the SAR temperature of healthy tissue cannot exceed that for harming healthy tissue, say in the upper 30's° C. or very low 40's° C.

$$SAR = \frac{\sigma E^2}{\rho_m} \quad (3)$$

where SAR is in watts per kilogram, and where a equals the bulk electrical conductivity (S/m), and $p_m$ is the mass density kg/m³, and E² is V/m.

Imaginary Part of Permittivity

Next, measured laboratory data empirical verifies the previous E-Field equations, trends, and dependencies. These tests show that the field-particle relationship is governed by definable and measurable results, where the results can be used to predict which nano-particle is responsive to which field, at what frequency, and to what relative heating level.

In FIG. 11, there are two sets of plots, both having the same material but of differing material concentrations. The material was tested using a Time Domain method to remove boundary artifacts to ensure the most accurate possible permittivity measurements. On the left side are two plots 1110, 1120 for a 10 mg/ml concentration of a surfactant, cocamidopropyl betaine. The upper left plot 1110 is the complex permittivity while the lower left plot 1120 is the product of epsilon zero, omega, and the imaginary part of the permittivity, same material, and same concentration. Plot 1117 in graph 1110 is the real part of the surfactant's permittivity, while plot 1112 in graph 1110 is the imaginary part. Water's real part is plot 1118 in graph 1110, and water's imaginary part is plot 1114 in graph 1110. We are interested in two things: the imaginary part value plot 1112 in graph 1110 and how that value relates to the imaginary part of water, plot 1114 in graph 1110. Thus, at around 3 GHz, the surfactant starts to separate going leftward from water (imaginary part plots). At 3 GHz, if the surfactant were in nano-form within the cancer, it would not heat any faster than the water in the surrounding tissue cells. At 1E08 or 100 MHz, water's imaginary part is virtually zero, meaning water does not heat at this frequency, while the surfactant is at 50 for its imaginary value, meaning it heats very rapidly at this frequency. Note that the imaginary part of the surfactant appears to go up asymptotically in plot 1112 of graph 1110. However, if the plot were extended to the left, it may come back down.

The Debeye plot for water is shown as plot 1114 in graph 1110. Water has a certain relaxation frequency of around 24 GHz (peak of plot 1114). If the molecule is larger, such as in surfactant, then the relaxation frequency is lower.

Figure 11A:
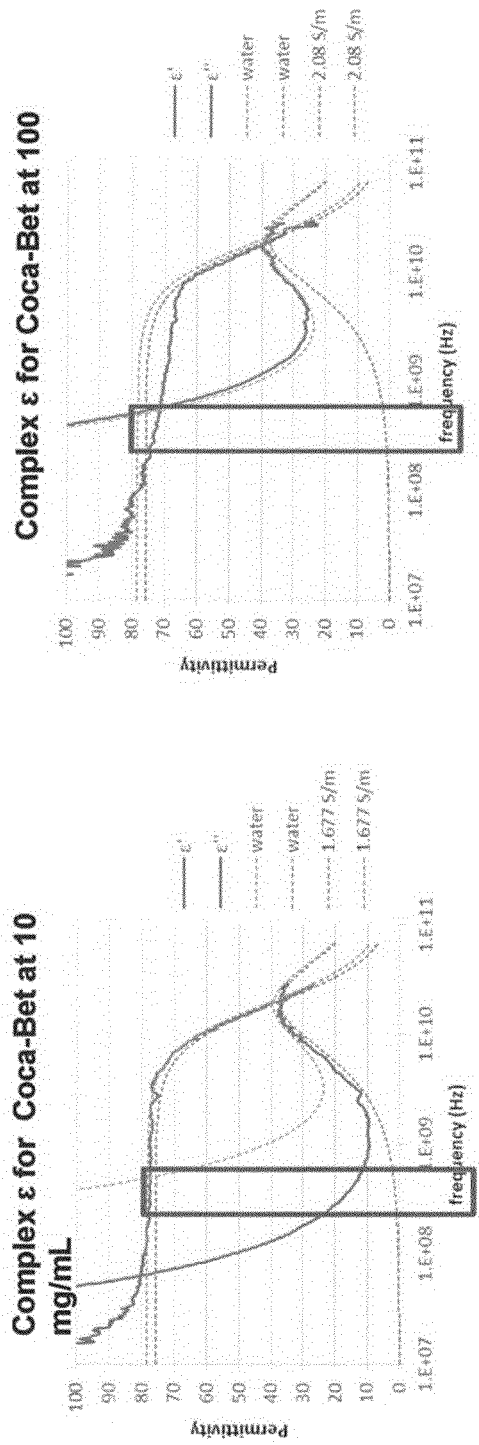
FIG. 11A illustrates the plots of FIG. 11 with an identification of two regions for discussion.

As the concentration is increased, as shown in the right hand graphs, upper right graph 1130 is 100 mg/ml for permittivity and lower right graph 1140 is 100 mg/ml conductivity, both for the surfactant. Note how the imaginary part of the surfactant in plot 1132 of graph 1130 shifts up and to the right. This means that, at a given frequency, the response is enhanced and, at higher frequencies, the response may become sufficiently different from water to be viable in terms of differential heating. Note also the real part of the surfactant plot 1137 of graph 1130 changed also. This is further illustrated in FIG. 11A by the vertical boxes. Note that, in the left plot, the imaginary part goes through the lower middle of the box; in contrast, on the right plot, the imaginary part just touches the right hand side at the top of the box and doesn't go through it. This is the result of the change in concentration from 10 mg/ml to 100 mg/ml.

Going back to FIG. 11 for a moment, only when plot 1112 in graph 1110 as compared to plot 1114 in graph 1110, and plot 1132 of 1130 compared to plot 1134 in graph 1130, having a substantial difference in value, do the nano-particles heat greater than tissue (which is largely water). Thus, the permittivity measurement test enables a very accurate assessment of whether a nano-material heats at all and whether it heats greater than the heating of water (or tissue). The next permittivity plot offers clarity to this concept.

Figure 12:
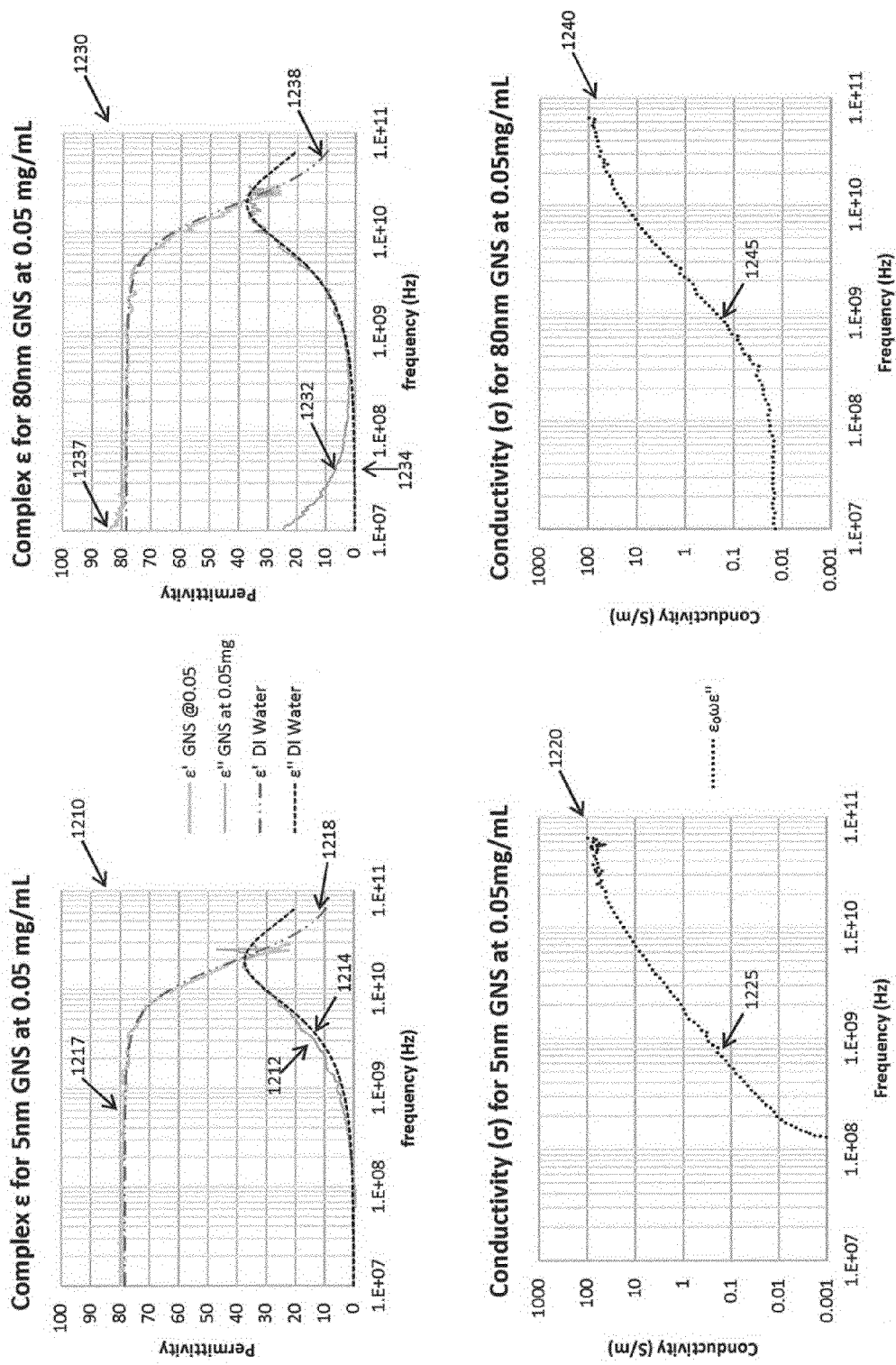
FIG. 12 illustrates a graphical representation of permittivity versus frequency for two sizes of gold nano-particles.

FIG. 12 shows permittivity measurements for gold nano-particles. The left-hand two plots 1210, 1220 are for gold nano-particles at 0.05 mg/ml for 5 nm gold spheres. The right-hand two plots 1230, 1240 are for 80 nm (nanometer) gold spheres with a same concentration of 0.05 mg/ml. Note that, for the left plot 1210, line 1212, the imaginary permittivity of the 5 nm gold spheres versus frequency, it almost exactly tracks the imaginary part for water line 1214 of graph 1210. This means that 5 nm gold spheres are not heated by an illuminating electric field from 10 MHz to 20+Ghz. In fact, this has been shown to be correct; laboratory excitations of 5 nm gold spheres do not heat at any frequency. In contrast, 80 nm gold spheres, upper right graph 1230, at line 1232, diverges from the imaginary part of water at around 250 MHz. Thus, at frequencies below 250 MHz, and more particularly at 10-30 MHz, 80 nm gold spheres get hot in an illuminating electric field. This is due to the non-zero imaginary value of the imaginary part of the permittivity of 80 nm gold spheres, with respect to water's imaginary part which is zero in this spectral region. In addition, where water has a zero imaginary value, it does not get hot, meaning tissue does not get hot.

Figure 13A:
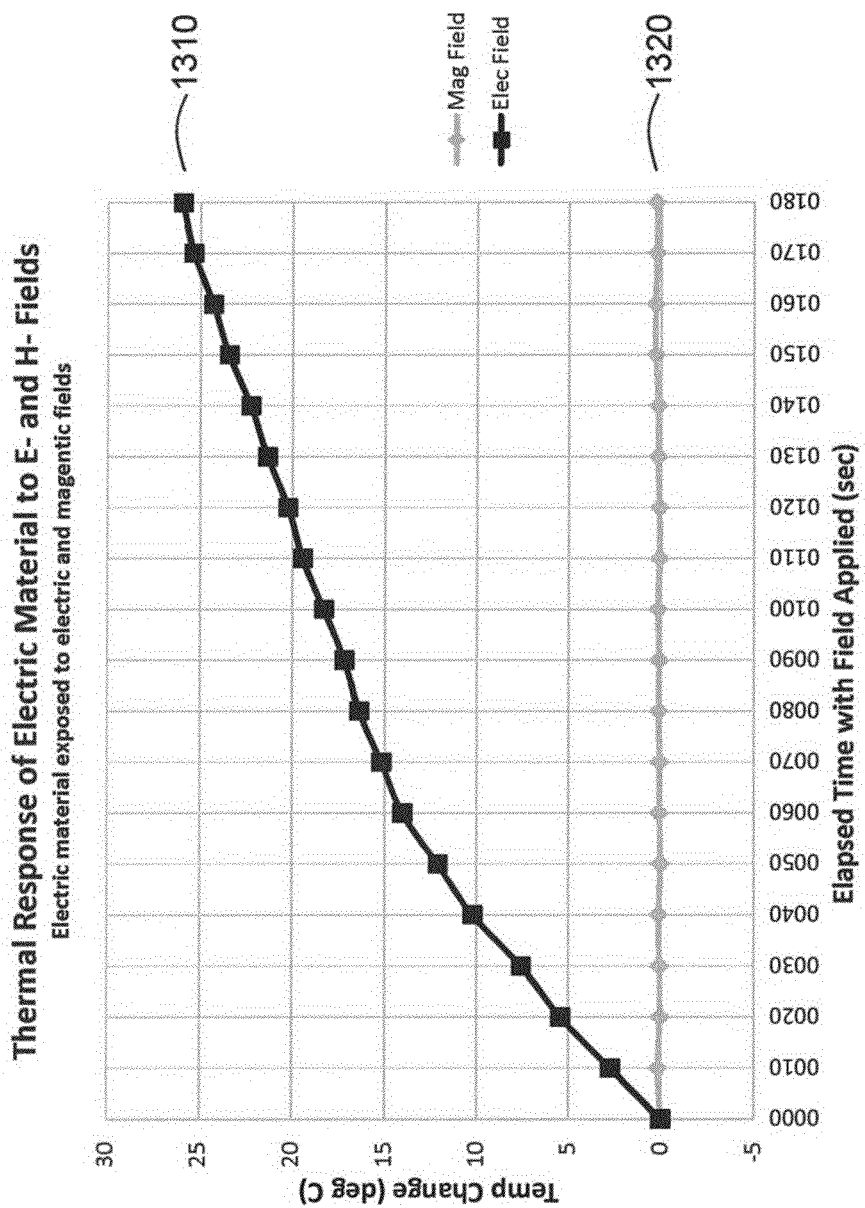
FIG. 13A illustrates a graphical representation of a surfactant in the presence of an electric field (strong response) and a magnetic field (no response)

FIG. 13A shows the responsive nature of materials is field dependent, sometimes in a binary manner. The material being tested is cocamidopropyl betaine. Plot line 1310 is the material thermally responding to an illuminating electric field. Over 180 seconds of time, the material's temperature is increased 26° C. Remember, to get to 43° C. where cell death occurs rapidly, it only takes around 6° C. of change. The electric field strength is 1,000 V/m (volts per meter), and the excitation frequency is 3200 MHz (or 3.2 GHz). Note that this material does not exhibit a rise in temperature in the presence of a magnetic field 1320. The frequency of the magnetic field is 290 KHz. Thus, a surfactant, having a non-zero value for the imaginary part of the permittivity, is only heated in an electric field and not a magnetic field.

Figure 13B:
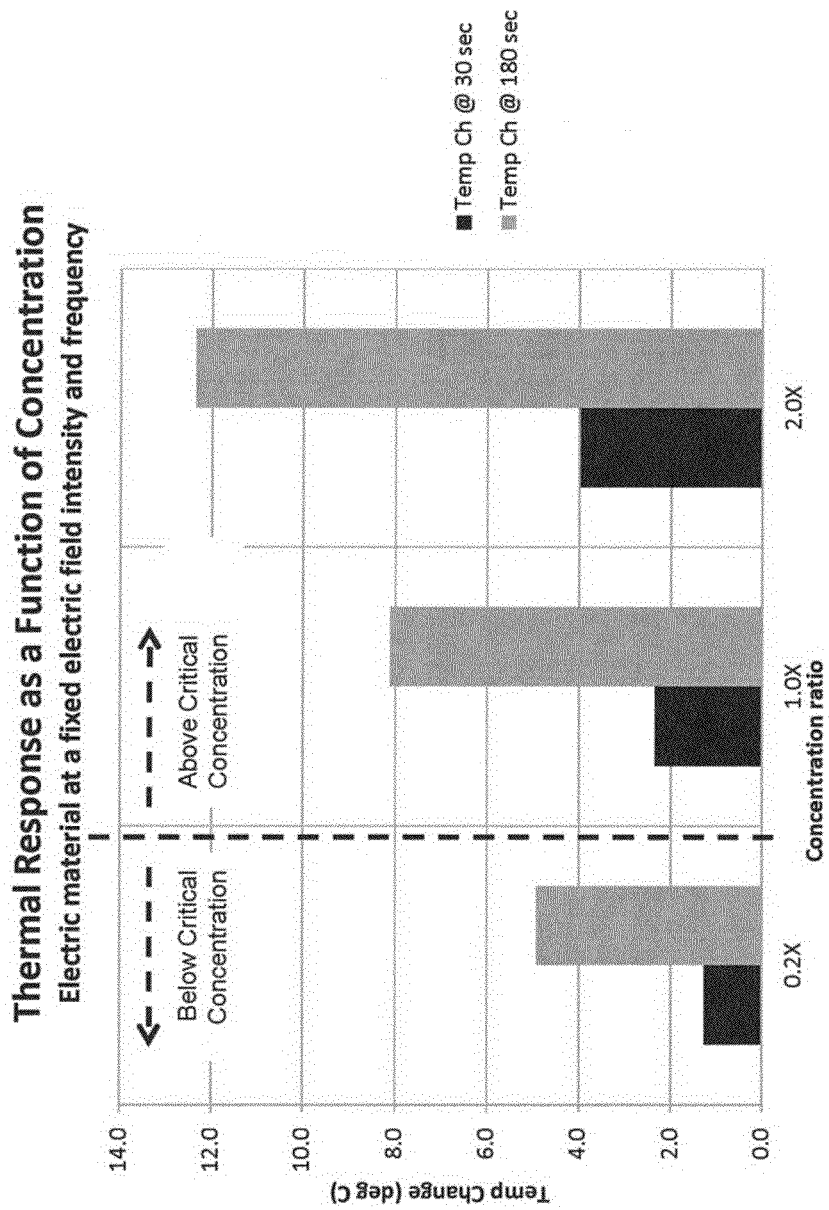
FIG. 13B illustrates a graphical representation of the effect of nano-particle concentration on induced temperature in an electric field using PEG200.

FIG. 13B illustrates the heating effect on a concentration of nano-particles. This is for PEG200 (polyethylene glycol) nano-particles in a 1,000 V/m electric field at 3200 MHz. For the 1.0× concentration, the 30-second temperature is a little over 2° C. At twice the concentration for 30 seconds, the temperature is just shy of 4° C., showing the linear heating relationship with particle concentration in an electric field. This is relevant to the level of particles that can be delivered to a cancer cell. If the concentration of nano-particles in the cancer cell is known, the illuminating field and time can be determined for a given temperature rise.

Figure 13C:
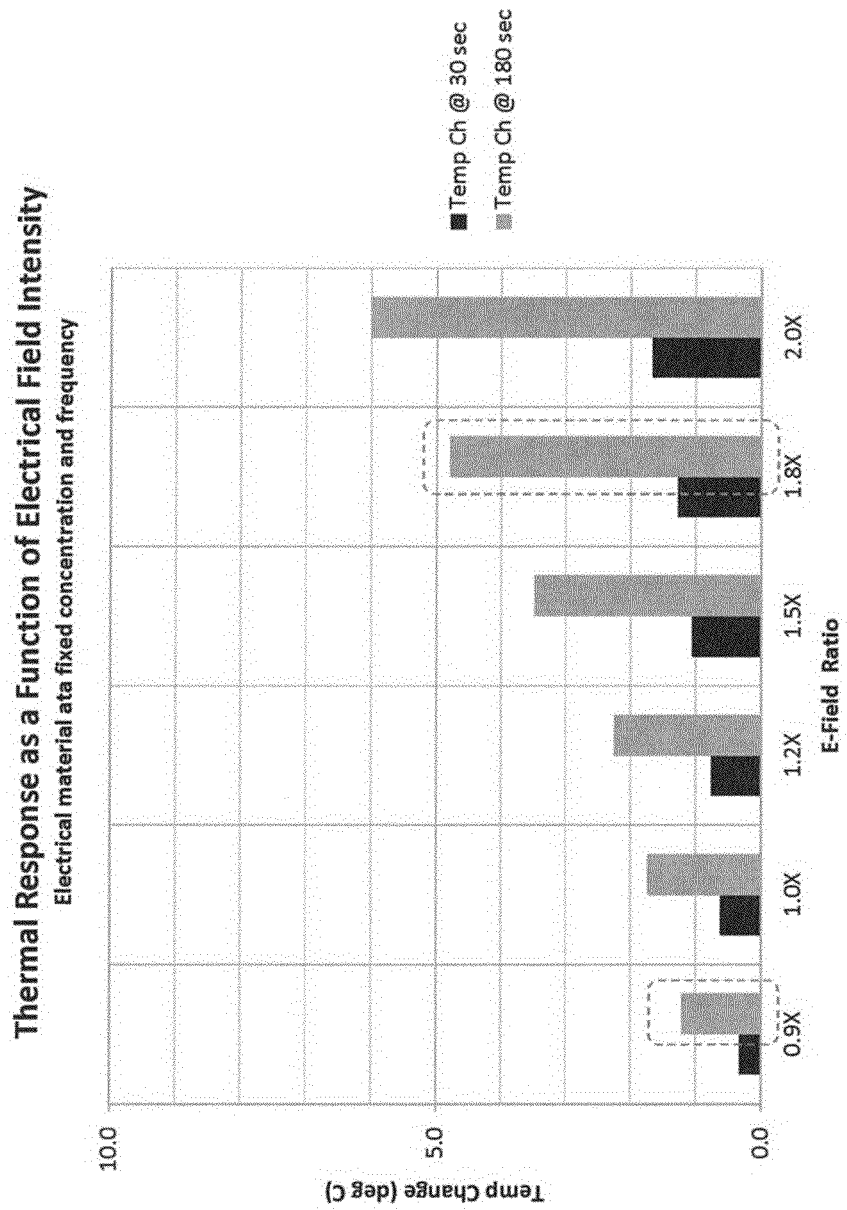
FIG. 13C illustrates a graphical representation of the nano-particle's temperature dependence on electric field strength for PEG200 in an electric field.

FIG. 13C illustrates the heating effect on a concentration of PEG200 nano-particles having a size of 1.65 nm to 2.001 nm. These nano-particles are in an electric field at 7,000 MHz (or 7.0 GHz). At 0.9× concentration, the field strength is 450 V/m; at 1.8× concentration, the field strength is 900 V/m. The temperature rise at 0.9× concentration is 1.2° C., while at 1.8× concentration, the temperature rise is 4.8° C. This is a temperature rise ratio of 4 times. Thus, when the field strength is doubled from 450 V/m to 900 V/m, the temperature increases by a factor of 4, or a squared relationship, as predicted by theory. The nano-particle concentration for this test is 1000 mg/ml.

Figure 13D:
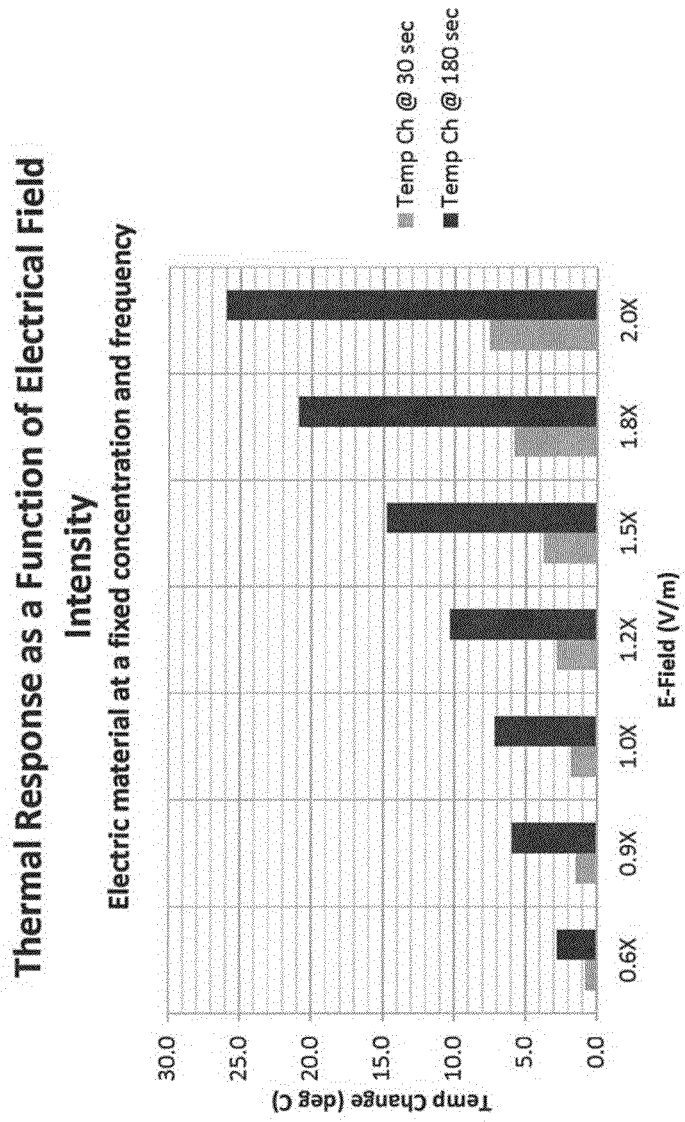
FIG. 13D illustrates a graphical representation of the temperature of a surfactant in different electric field intensities.

FIG. 13D illustrates the thermal response as a function of electric field intensity, and 13E illustrates the temperature change as a function of the applied electric filed.

Figure 13E:
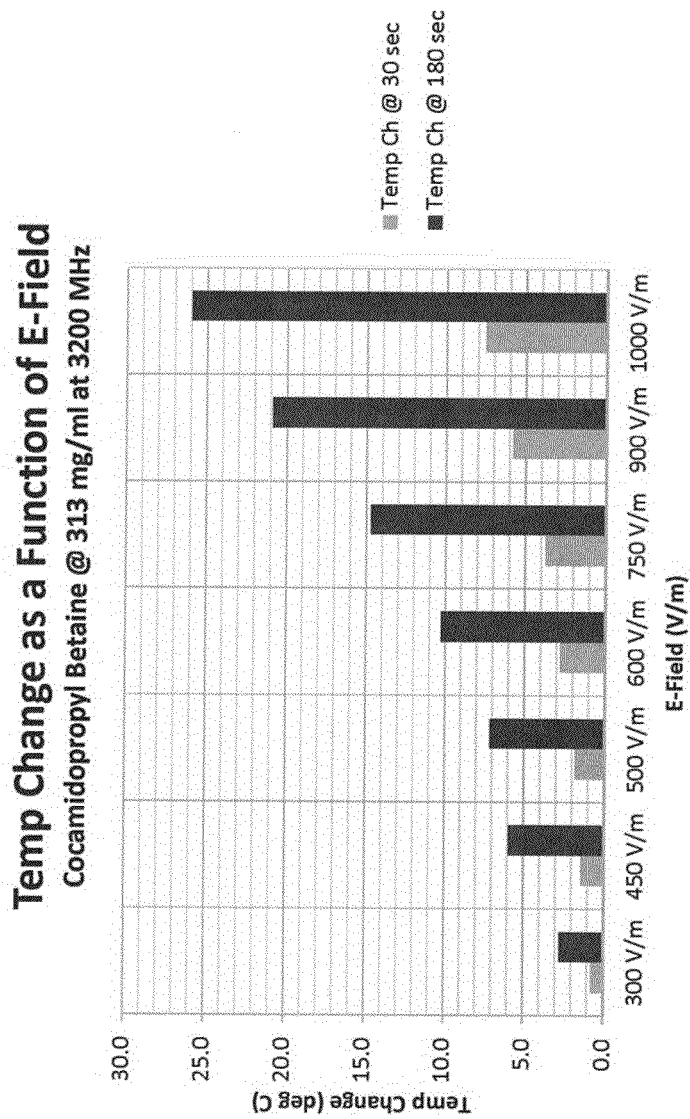
FIG. 13E illustrates a graphical representation of the temperature of a surfactant in different electric field intensities as shown in FIG. 13D, labeled to show the actual values of file parameters.

FIGS. 13D and 13E illustrate the response of the surfactant cocamidopropyl betaine at a concentration of 313 mg/ml at a frequency of 3200 MHz. The field strengths are shown in FIG. 13E. Note the non-linear shape of the temperature curves for different field strengths. If we look at 500V/m or 1.0× electric field strength (7.0° C.) compared to 1,000 V/m or 2.0× electric field strength (26.0° C.), for 180 seconds, we see the temperature ratio is around 3.7 times. At 30 seconds, therise in the temperatures of the cocamidopropyl betaine in the different electric fields are 1.9° C. to 7.5° C. or a ratio of 3.95. Thus, within experimental error, the squared temperature rule for a doubling of field strength applies to a surfactant.

Figure 13F:
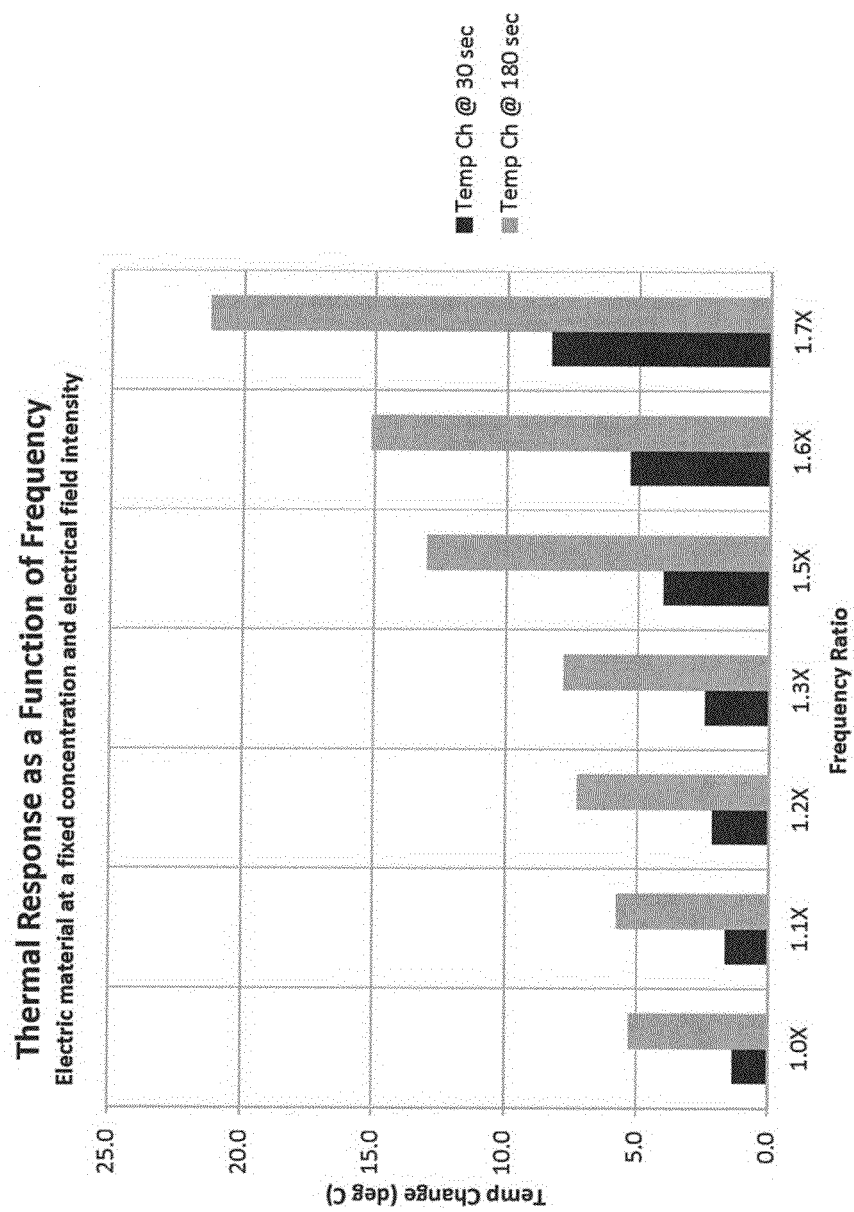
FIG. 13F illustrates a graphical representation of the PEG200 nano-particle's heating dependence on the exciting energy field frequency.

FIG. 13F illustrates a plot of the thermal response of PEG200 nano-particles in an electric field of 1,000 V/m with a concentration of 1,000 mg/ml as a function of the frequency of the applied electric field. The frequency heating dependence stated by the equations is dependent on the excitation frequency in combination with the value of the imaginary permittivity at the stated frequency; the measured results here suggest something at least squared or likely greater. From a 5.3° C. temperature rise at 1.0×, the baseline frequency (180 second plot), to 21.5° C. temperature rise at 2.0×, the baseline frequency (180 second plot), this has a ratio of 4.0. At 1.0×, the baseline frequency (2.2 GHz) and at 1.7× the baseline frequency (3.7 GHz), the rise in temperature ratio was 4 times for a 1.7 times change in frequency, suggesting a relationship greater than a squared one.

Magnetic Field—Particle Data

Figure 14A:
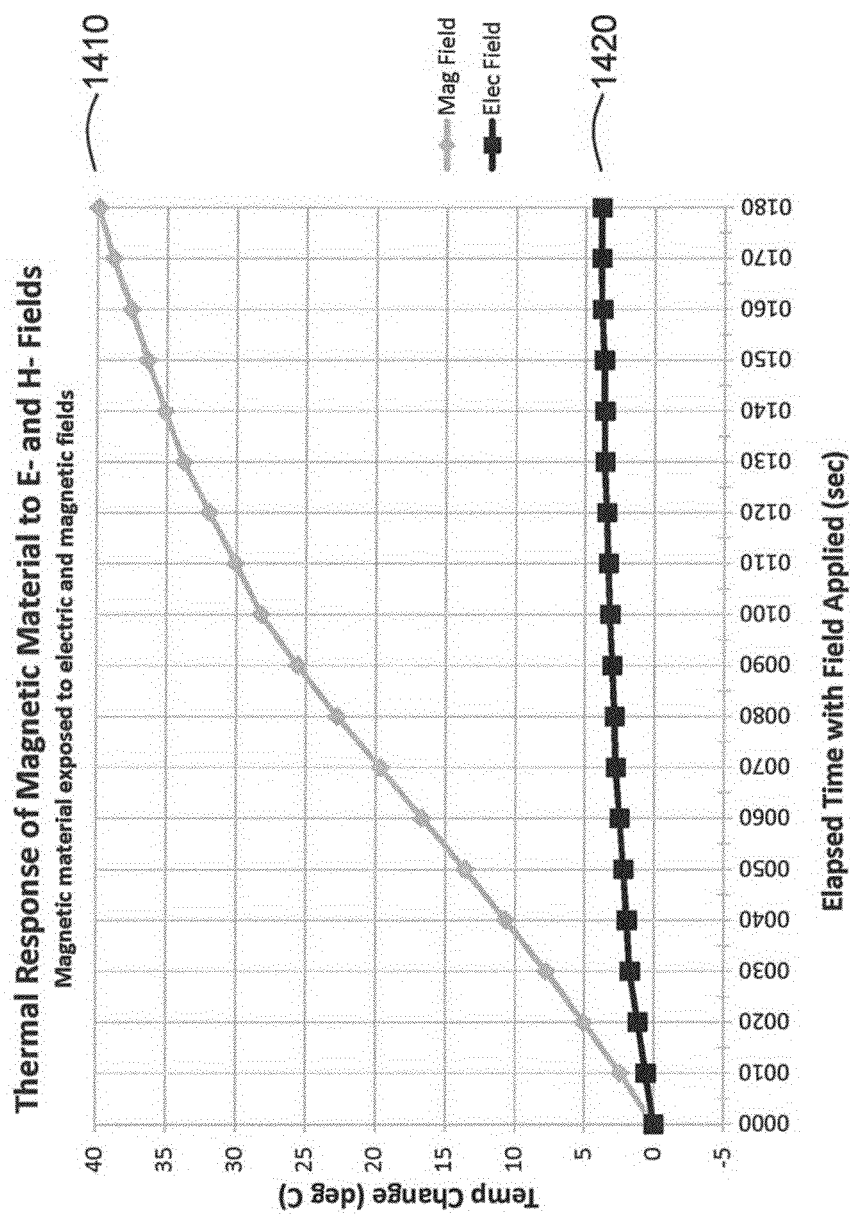
FIG. 14A illustrates a graphical representation of an $Fe_3O_4$ iron oxide nano-particle in both magnetic and electric fields where the nano-particle only thermally responds to the magnetic field.
Figure 14B:
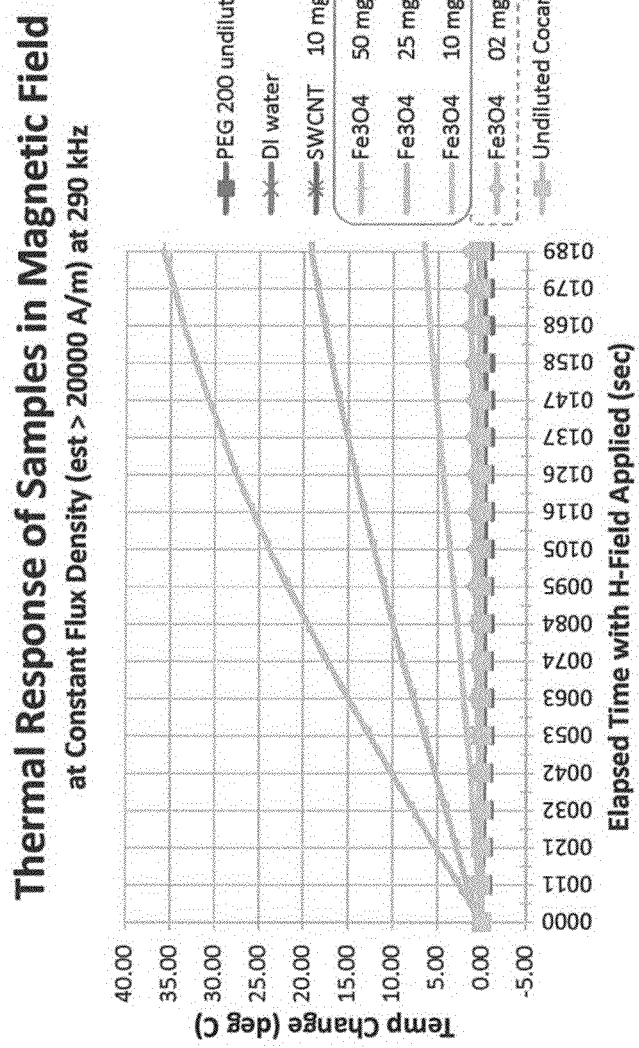
FIG. 14B illustrates a graphical representation of a number of materials in a magnetic field, where only the iron oxide responds to the magnetic field with a temperature increase.

FIG. 14A shows a plot of one material, iron oxide $Fe_3O_4$, in both a magnetic field and an electric field. The nano-particle concentration is 50 mg/ml. The magnetic field frequency is 290 KHz. This is plotted as line 1410, which shows a strong thermal response to being exposed to a magnetic field—upwards of 40° C. temperature change at 180 seconds. In contrast, this material does not heat in an electric field, line 1420. The E-Field is at 3.2 GHz at 1,000 V/m. There is a light temperature rise of 1420, but this is because the iron ferrite particles are in a colloidal solution of water. It is the small portion of water that is actually heating here versus the nano-particles. Thus, like the electric field example in FIG. 13A, the nano-particle can exhibit very selective heating based on the correct pairing of the field-to-particle relationship.

In FIG. 14B, again in a magnetic field of around 20,000 A/m, only the iron ferrite (circled boxes and upper three plotted lines) gets hot. Note that the iron ferrite of 02 mg/ml barley moves in temperature; that is because, like for the electric field, there is a minimum nano-particle concentration necessary to get the particles to begin heating. In this case, 2 mg/ml is too low and it doesn't heat.

Figure 14C:
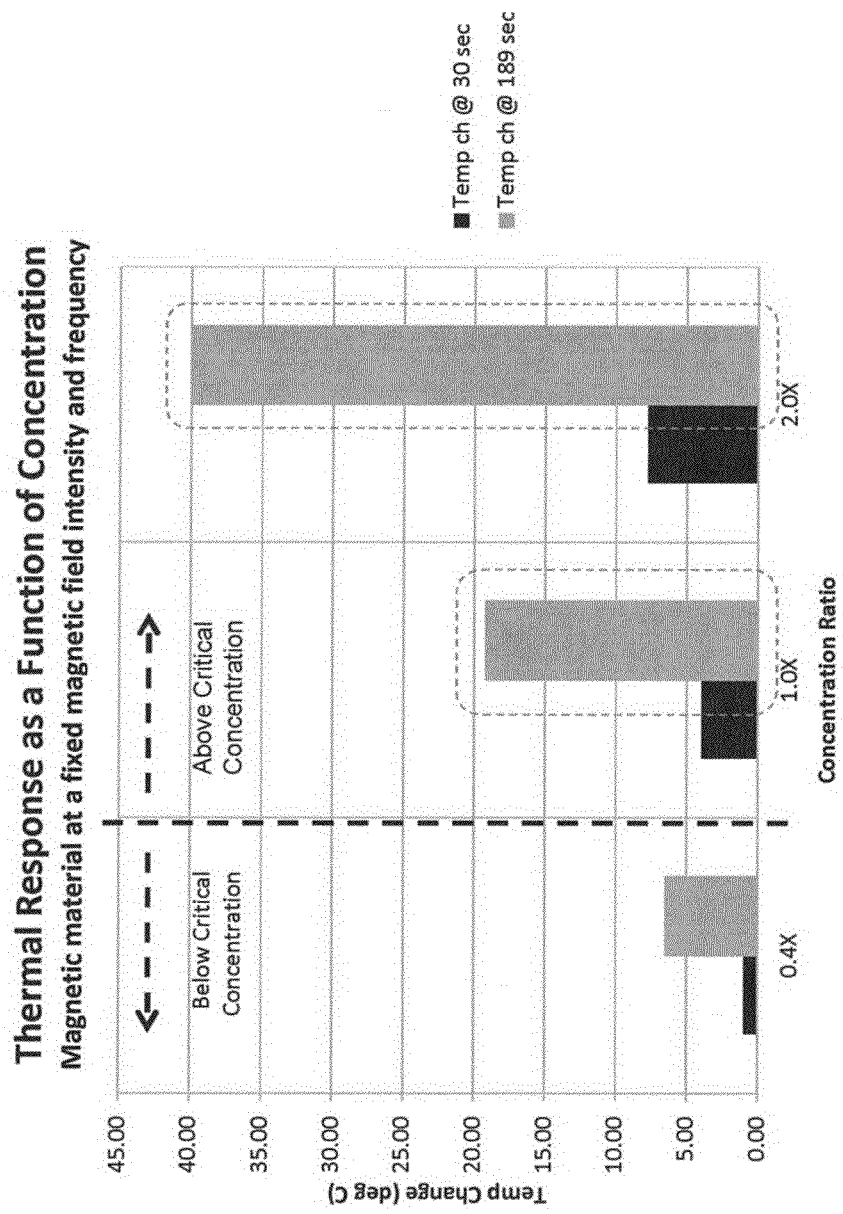
FIG. 14C illustrates a graphical representation of the temperature dependence of iron oxide at different concentrations in a magnetic field.

FIG. 14C shows the linear relationship effect of concentration when using a magnetic field and nano-particles susceptible to magnetic fields. Again, the particle is $Fe_3O_4$ and the nano-particle size is around 55 nm. The excitation frequency is 340 KHz. For the two dashed boxes outlining the two bar graphs, at a 1.0× concentration, the temperature is around 19.2° C.; at 2.0× concentration, the temperature is at 40° C. This is a ratio of 2.08 or effectively a linear relationship. Thus, like the electric field data set, the magnetic field versus particle relationship is a linear one with respect to particle concentration.

Figure 14D:
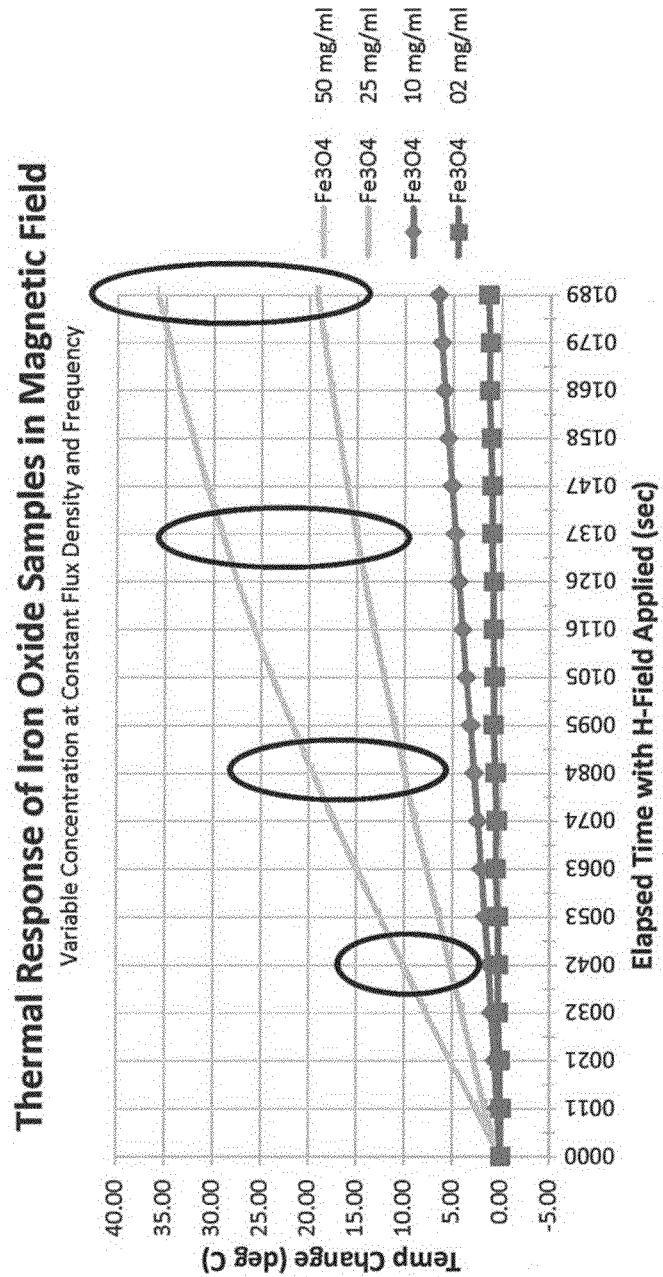
FIG. 14D illustrates a graphical representation of the temperature dependence of iron oxide at different concentrations at different point in the heating cycle time frame.

In FIG. 14D, there are four sets of circled data point pairs, between a concentration of 25 mg/ml and 50 mg/ml. For all four of these pairings, the temperature relationship is a factor of two. Thus, this confirms FIG. 14C—the temperature rise is linear with a change in nano-particle concentration. Again, like the electric field example of concentration, the importance of this relationship is actually at a cellular level; that is, how many nano-particles are delivered to a cancer cell. The excitation temperature is dependent on how many particles arrive at a given cell. The more particles, the hotter the cancer cell will get. Alternatively, if a given nano-particle administration protocol is known to deliver X particles per cell, then, the excitation function, time/field strength/frequency can all be pre-determined a priori to actual treatment.

Figure 14E:
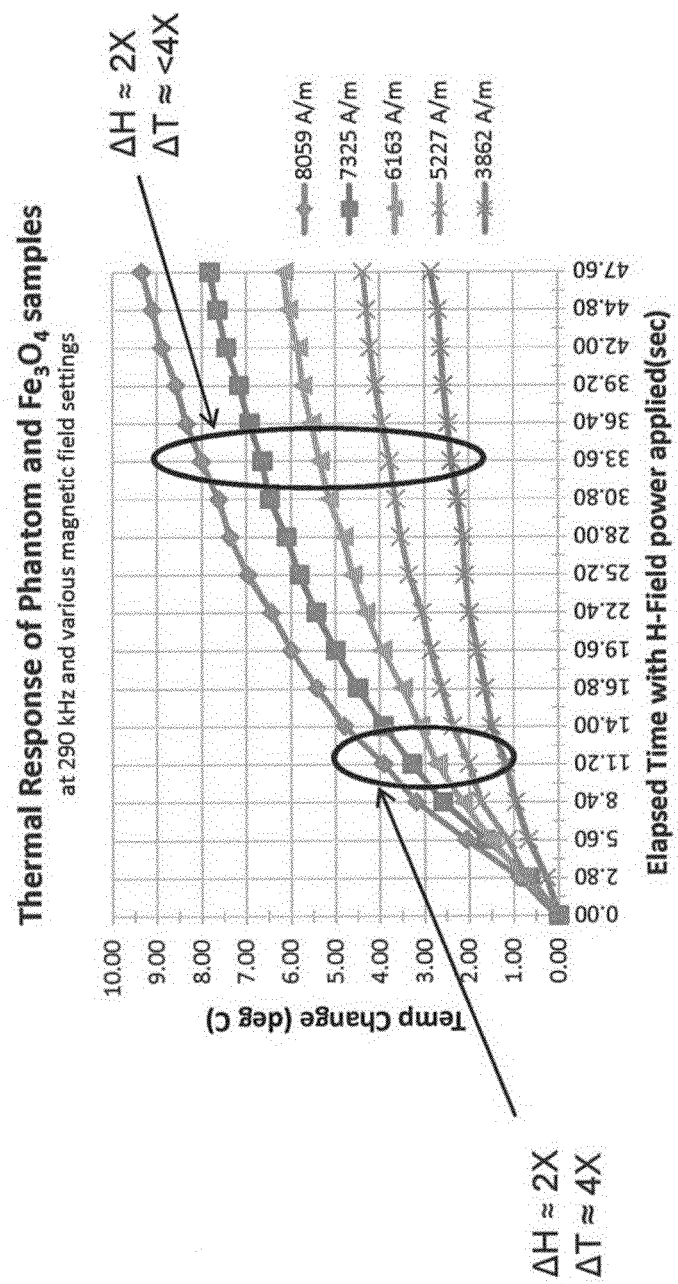
FIG. 14E illustrates a graphical representation of the iron oxide temperature dependence on field strength and on the duration of the illumination.

Now we look at magnetic field strength. FIG. 14E shows a test of varying magnetic field strength. This is using nano-particles that are composed of $Fe_3O_4$ at 25 mg/ml at 290 KHz excitation frequency. The nano-particles were placed within a material that emulated the electrical characteristics of human muscle at the given frequency. The two black circled regions show a ratio of on the low end 1.0° C. to 3.9° C. (ratio of 3.9) to on the high end 2.2° C. to 8.0° C. (ratio of 3.6). This is for a field strength change of almost 2 times, which produces a temperature change of close to 4 times, thereby experimentally confirming the field squared relationship on heating in the magnetic domain. This holds similar to when the electric field is squared and the temperature goes up by a factor of 4 times.

Magnetic Field Heating

In general, there are three types or regions of magnetic heating: Brown, Ned, and Rayleigh. The Brown region is at lower frequencies, and the heating is caused by the magnetic nano-particle physically rotating in the medium, such as in a cancer cell. Since the Brown region is at such a low frequency, not much heating energy can be imparted using this mode. The Ned and Rayleigh regions are characterized by the creation and relaxation of magnetic domains or dipoles in the nano-particle itself. When the magnetic domains or dipoles are random and then forced to become ordered and then random again, as when occurs in an alternating phase magnetic field, heat is released by the nano-particle. Both the Ned and Rayleigh regions are much higher in frequency than the Brown region, and the nano-particle itself does not rotate.

The Ned region, for a variety of reasons not discussed herein, is extremely sensitive to the size of the nano-particle in terms of the highest heating state with respect to the excitation frequency. Thus, a log normal distribution of nano-particle sizes would mean that only a portion of the nano-particles, say 45%, would be optimally heated. The falloff rate of heating is orders of magnitude: an example would be a change of nano-particle size by 4-5 nanometers results in a heating change of up to four orders of magnitude. This is not optimal for single frequency illumination if the nano-particle sample size is not tightly controlled. One possible positive or advantageous use of this characteristic is to use nano-particles that have two different sizes, which are targeted to two different material types, where the nano-particle size distribution is tightly controlled. The excitation then is done at two different frequencies sequentially applied with a waiting period between each excitation. The two regions or extents of nano-particles, located in healthy tissue vs. cancerous tissue, then could be easily mapped.

For a broader size distribution of nano-particles, a more broadband frequency magnetic field is required to ensure that all the nano-particles are heated. In this manner, the log normal nano-particle size distribution is still optimally heated because the excitation frequencies are broadband, thus ensuring that all nano-particles have the optimal frequency. The selected frequency spectrum should match the nano-particle size distribution so the time or temporal space for a given frequency matches the relative number of nano-particles for that given frequency.

Alternatively, if the nano-particle sample size distribution is highly varied and cost implications make it difficult to tighten this up (it is difficult and costly to get 100% of the nano-particles exactly at a 20 nm diameter for instance), then working in the Rayleigh region removes this size vs. frequency dependence. There is also some evidence that suggests that heating of the magnetic nano-particles in the Rayleigh region could be an $H^3$ function, which would clearly be advantageous.

It is clear that nano-particle heating in the Rayleigh region is less dependent on nano-particle size, as it is in the Neel region. As discussed, this could be both an advantage and a disadvantage. The advantage is that it removes the nano-particle size dependence on frequency for heating, meaning the nano-particle size distribution can be less tightly controlled (lowering the cost of the nano-particle). On the flip side, the disadvantage is that the ability to use nano-particle size as a differentiator in the heating process is now gone, where one size is used for healthy tissue and a second size is used for cancerous tissue, each having their own optimal heating frequency.

When using a pure magnetic field (H-Field), tissue heating is generally very low, almost non-existent, provided the product of frequency and A/m magnetic field strength is kept below certain levels where eddy currents, hence heat, are introduced to the body. This product has been experimentally determined to be $4.85*10^8$ where, after an hour at these levels, human subjects have suggested they were feeling "warm-ish" in the illuminated region. Clearly, an image can be extracted much faster than that timeframe, especially when magnetic field susceptible nano-particles are used, such as iron ferrite, where 45 nm iron ferrite $Fe_3O_4$ nano-particles have been heated to very high temperatures of 90° C. in a matter of 180 seconds. For the differential temperature imaging method, the temperatures needed are significantly lower since the body is around 37° C.

Equations 4 and 5 govern the power absorbed (in watts) by a nano-particle in the presence of a magnetic field. Like the equations for the electric field contribution to power absorbed, the magnetic field power absorbed contribution is a function of the field squared ($H^2$) and a linear effect with angular frequency, ω, in addition to the effect of frequency on the imaginary part of the relative permittivity. Similar frequency dependence and field strength dependencies exist with the magnetic field. For conductors, surface charges at the interface prevent the electric field from penetrating efficiently in the metallic particle. This "screening" occurs at a scale defined by the Thomas-Fermi length. This is not dependent on skin depth. However, in contrast, the magnetic fields are continuous at the interface and, therefore, can penetrate into the material itself (a conductor). Nano-particle conductors, in general, are best paired with a magnetic field.

In general, materials that are conductors or have free electrons are best illuminated by a magnetic field. An exception would be aluminum, which is not responsive to magnetic field heating. Molecular compositions that have an even number of oxygen atoms, such as Fe and $Fe_3O_4$, are best heated with a magnetic field.

$$P^M_{abs}(\omega) = \omega 2\mathrm{Im}(\alpha_H) \quad \mu_o \frac{<|H|^2>}{2} \quad (4)$$

$$\alpha_H = \frac{2\pi}{15}R^3\left(\frac{2\pi R}{\lambda}\right)^2 (\varepsilon_r - 1) \quad (5)$$

The magnetic field does not heat tissue like the electric field does because the magnetic field has no impact on materials that are dipolar or exhibit a strong permittivity. This has inherent advantages in terms of creating a detectable heating difference between healthy tissue and cancerous tissue where nano-particles reside.

There are empirical and theoretical equations that describe the heating of nano-particles for each of these three regions. For brevity, these equations are not included herein.

Both Sets of E and H Equations

The above-presented sets of equations have a dependence on nano-particle size. The electric field heating has an $R^3$ dependence, while the magnetic field has an $R^5$ dependence. Thus, for very small nano-particles, 5 nm (nanometers) and below, the imaginary parts of the E and H equations (Equation 1 and Equation 4, respectively) are almost identical. However, as the particle size increases to 10 nm and bigger, the magnitude of the imaginary part of the H-Field becomes bigger than the E-Field. One example, calculated at optical frequencies, has the magnitudes of the two respective components alpha E and alpha H varying by an order of magnitude (10 times).

Materials that work well in both fields are those that have a physical distribution in a powder form of two substances, such as zinc oxide—cobalt (ZnO—Co) in a composite sample. For example, when in the E-Field, the ZnO heats to high temps (900° C.) while the cobalt only goes to 50° C. In a magnetic field, the cobalt heats to 700° C. while the ZnO (zinc oxide) only goes to 50° C. Thus, an electro magnetic field (EM) heats both substances to their respective highs of 900° C. for zinc oxide (ZnO) (from the electric field portion) and 700° C. for the cobalt (CO) in the magnetic field portion of the composite EM wave.

Material Properties

The heating of tissue is dispersive with frequency; as the frequency changes the relative permittivity and conductivity of the tissue changes. Different tissue types have different permittivities and conductivities, again changing with frequency. Cancer also has its own dispersive electrical properties, which are unique. This is yet another method of particle location detection, or cancerous vs. healthy tissue detection.

By using a very broadband illumination source, such as UWB or Ultra-Wideband energy, the material properties change significantly from the lowest frequency to the highest frequency—these material properties can be detected and spatially mapped. Thus, the material properties greatly differ from F(low) to F(high)-, for healthy tissue, for cancerous tissue, and for nano-particles. These differences in material properties offer a means to distinguish and spatially map the cancerous regions containing nano-particles.

Particle Properties

Characteristics of particles include size, shape, material composition, density, surface coating, geometry, contents, and behavior in the presence of an energy field have predetermined characteristics. In addition, the data can contain a listing of cancer types for which the particular target particle is effective.

FIG. 2A is an example, in table format, of target particle characteristics for nano-particles. These particles are for Ablation versus Low Temperature Hyperthermia. For example, for a predetermined model of nano-particle (ex.—9736C) there are relevant characteristics, such as: geometry (cylinder); material which is used to fabricate the nano-particle (IronOxide); dimensions (10 diameter, 75 length); coating (PEG, Poly Ethylene Glycol); concentration (85 picograms per cell (per cancer cell)); and excitation response function of 1000 V/m and 15000 A/m. Two fields are used since the nano-particle has two materials which are susceptible to differing field types: the iron ferrite $Fe_3O_4$ is susceptible to a magnetic or H-Field only (given in A/m), while the PEG coating is susceptible to an E-Field only (given in V/m). The frequency for the E-Field is in the upper S-band range, or 2.5 to 3.0 GHz, while the magnetic field is lower, in the MHZ range, 14 MHz. These selected frequencies are representative and in no manner are limiting. For example, the magnetic field could be in the 200-300 KHz range, where heating has shown to be very responsive. Frequency selection is chosen based on the area being treated, the particle type, the level of reflections and penetration depth, and so on. For instance, selecting the magnetic frequency extremely low puts the magnetic excitation in the Brown region, which does not induce as much energy into the nano-particle, hence, heat into the tissue. For some cases, this may be desirable on the Imaging side of the process, but less desirable on the Treatment side of the process. At frequencies that are not resonant for the nano-particles, frequencies in the MHz or GHz region, the illumination polarization is less important, since nano-particles are resonant in the terahertz region (light spectra). However, the illumination polarization for tissue does have importance; and certain tissue artifacts may show up using different polarizations. At optical or laser excitation, the nano-particle shape and size become important, since the nano-particle size becomes a substantial part of the illuminating wavelength. In addition, at optical or laser frequencies, nano-particles can begin to exhibit meta-material behaviors such as SPR, or Surface Plasmon Resonances. The excitation phase can be controlled to ensure that all energy impinging on the skin, for example, arrives in phase so it is additive. In other cases, the electrical phase of the energy can be adjusted to steer the exciting beam over the region to illuminate, thereby causing a moving energy field over the breast, for example.

Other nano-particles such as 6754Z in FIG. 3 are designed to have an enhanced acoustical response when excited with an energy pulse, RF/microwave, or optical. The PEG shell is more easily compressed since it has a surfactant filling (fluid-like filling) thereby being more easily compressed/expanded and thereby emitting a stronger acoustical response which is unique from either healthy tissue or cancerous tissue. This material is also unique in terms of its permittivity and conductivity in an E-Field or E(M)-Field.

These entries define the responsiveness of the selected nano-particle to a preferred applied energy field, as well as the physical and chemical characteristics of the nano-particle that can be used with a particular invasive agent. For example, a nano-particle of long linear aspect ratio, long and skinny, often is susceptible of being consumed by a cancer cell, yet also is too large or shape specific to be excreted by the cancer cell. A coating of carbodilimide conjugated polyethylene glycol-iron oxide-impregnated dextran can be used as the "composite" deposited on the nano-particle to make it attractive to human breast cancer cells.

Energy Fields

An energy field is comprised of fields in the electromagnetic spectrum which range from kilohertz to optical frequencies (terahertz). Radio Frequency (RF) and Microwave energy is contained within this spectrum. The fields can follow or be bounded or be explained by Maxwell's equations, and they can exhibit quantum behavior (light, for example, exhibits both wave and quantum particle behavior simultaneously). The innovation described herein focuses on electromagnetic energy that exhibits more wave-like behavior. However, it should be noted that the nano-particles that are being excited by the Maxwellian waves may themselves exhibit linear or stepped behavior (which is quantum like in its nature). So, while the illumination function is described by Maxwell's equations, the nano-particle, which is activated under the Maxwellian illumination, may very well exhibit behavior that is non-linear in its nature.

The Maxwellian fields used for illumination functions generally can take the form of three types of fields: an electromagnetic field (EM) which has both types of waves, magnetic and electric, in a spatially orthogonal relationship; an electric field (E); and a magnetic field (H). It is important to recognize that any combination of these three basic field types are possible; and, in fact, may be desirable. Thus, the illumination may be multifold vs. a single illumination type. In addition, the combinations of fields can be arranged to include spatial and temporal domains. Therefore, it is possible (for example) to have a magnetic field for 2 seconds, followed by an electric field for 5 seconds, in a time or temporal sequential fashion. As another example, 65% of the illumination space could be covered by an electric field while the entire illumination space is illuminated by a magnetic field, all in a concurrent fashion; or a baseline electromagnetic field (EM) could illuminate the target region with a pulsed magnetic field covering the same region. Separately, a given illumination function may only be the electric field, or it may only be the magnetic field, or it may only be an electromagnetic field. Nothing contained herein limits the possibilities or modes of illumination by given field types.

An example of both field types, E and H, being concurrently active is an electromagnetic (EM) field; and a further example is an electromagnetic wave that is propagating through the air carrying a signal, with both field types, electric E and magnetic M. In an EM wave, the electric and magnetic fields are spatially orthogonal to each other and propagate together. In contrast, a "pure" electric field has an electric field only and a "pure" magnetic field has a magnetic field only. As already described, an electric field is denoted by the letter E, while a magnetic field is denoted by the letter H, while an electromagnetic field is denoted by EM.

When a material is illuminated by a given energy field type, the material "absorbs" energy from the field and exhibits that "absorption" by exhibiting a temperature rise, or converts the field to an electrical current, or exhibits other modes of excitation such as an electro-fluidic force, mechanical motion, and so on. The pairing of the target particle type and the energy field type is managed to control or produce by design a given behavior in the target particle. One desirable illumination energy field-to-target particle trait or property is the presence of a thermal rise in the target particle. When the target particle is placed in an energy field, the target particle, through a mechanism described in the following sections, exhibits a thermal rise to a higher energy state. The thermal rise in the target particle is highly dependent on the pairing of the composition of the target particle (including size, shape, material composition, density, surface coating, geometry, contents, or behavior in the presence of an energy field having predetermined characteristics, etc.) with the illumination function, E-Field, H-Field, or EM-Field. Another desirable trait in the particle under illumination is the propensity to exhibit a strong acoustical response such as that when illuminated via a pulse of energy, RF/Microwave, or laser. In the first case, thermal, this delta increase can be mapped and used to differentiate the cancerous tissue with particles vs. healthy tissue. In the second case, acoustical response from material compression/expansion would be used to enhance or differentiate the acoustical signature of both healthy and cancerous tissue from cancerous tissue containing nano-particles.

Target particles contained within a given energy field exhibit certain behaviors. Most important, different target particles and their associated composition respond uniquely in a given energy field type. In fact, certain target particles do not respond to a specific field type whatsoever; that is, no energy is absorbed by the target particle in that given energy field. An example is a target particle formed of zinc oxide responds dramatically to an electric field with a sharp temperature rise but has virtually no thermal response to a magnetic field. In contrast and in converse, a target particle formed of $Fe_3O_4$ (iron oxide) exhibits a very steep temperature rise in a magnetic field and has virtually no temperature rise in an electric field. Target particles manufactured from other materials respond in varying degrees to either E- or H-Fields. Target particles manufactured from copper, for example, respond almost equally to either energy field type, E or H. For materials that respond to both E- and H-Fields (such as copper), an optimal excitation source may be an electromagnetic wave (EM), since it simultaneously contains both energy field types in an orthogonal configuration.

Thus, the energy field type used for heating materials needs to be optimally matched to the composition of the target particle. Existing prior art does not recognize the importance of this pairing, that is, the pairing of illumination energy field type to composition of the target particle.

It is even more important to precisely pair the energy field type for nano-particles, because they have virtually no mass, to thermodynamically convert their "absorbed" energy to heating of tissue where the nano-particles are residing. Without this precise pairing of illumination function with nano-particles' material type, the nano-particles do not reach a high enough temperature to thermodynamically transfer their thermal energy to surrounding material (cytoplasm, nucleus, membrane). Separately, the physical composition of the target particle (size, shape, material composition, density, surface coating, geometry, contents, and behavior in the presence of an energy field having predetermined characteristics) makes a difference in how the target particle behaves under illumination. The concentration of the energy field strength is an important parameter. In fact, equations show that the heating phenomenon is a function of the energy field strength squared. This is true for both E- and H-Fields, with H-Field illumination being driven by even more complex equations, where sometimes the function could move up to an H-cubed relationship. This cubed relationship has been proposed for specific, unique circumstances by some authors. Thus, for example, devices that realize "induction heating" methods, which use a very concentrated H-Field, heat metals to melting points, while a more distributed H-Field won't have the same heating effect. Therefore, how the field is constructed and presented or delivered to the body or tissue is an additional parameter that is important and controllable.

The prior art has extremely limited understanding of the mechanisms occurring in terms of the thermal heating or other processes of nano-particles in fields of any type. This rather blind approach, presently in use, has no design consideration of energy field/target particle pairing optimization whatsoever.

Low Temperature Hyperthermia Particles

The Low Temperature Hyperthermia method uses specially designed nano-particles that exhibit a specific temperature rise in a given illumination energy field and then have no further temperature rise even if the applied illumination energy field increases beyond the optimal level. Alternatively, the nano-particles exhibit a tightly controlled temperature rise based on a pre-determined or pre-designed a priori temperature rise for a given illumination energy field strength. The illumination energy field that is applied is either an electric field (E-Field) or a magnetic field (H-Field) or a combination of both, as an E- and H-Field or via an orthogonal field such as an EM-Field. The nano-particles exhibit the property of not getting any hotter than a pre-determined, pre-designed temperature even if the exciting illumination energy field strength continues to rise. This ensures that an optimal temperature, which for the purpose of this description is selected to be 42° C., is not exceeded in the tissue which minimizes the release of Heat Shock Proteins while further stressing the cancer cells so that they die, versus emitting cancer stem cells/other cells. It also ensures that healthy tissue is not harmed, should an errant nano-particle end up in healthy tissue. This treatment approach is called Low Temperature Hyperthermia.

This Low Temperature Hyperthermia System first uses radiation or chemotherapy to kill the majority of the cancerous cells followed by the application of E-Field or H-Field or EM-Field radiation with on-site nano-particles to realize a temperature rise to 42° C. in the cancer cells. The advantages realized by this treatment protocol are significant: virtually any tumor location can be treated; the release of Heat Shock Proteins is minimized (at 42° C.); an errant nano-particle in a healthy cell will not harm a healthy cell at 42° C.; and cancerous cells are kept at a nominal 42° C. (or some other optimum temperature) to ensure that the already stressed cancer (from radiation or chemotherapy) is continuing to die and that cancer stem cells are not released. Separately, a third killing element can be added—if the nano-particle is a temperature sensitive liposome, the liposome shell will "melt" at a design temp which is less than 42° C., wherein a cytotoxin can be released. This third killing method, the released cytotoxin, is the third step of a multi-pronged approach to kill deep seated cancer tumors.

The Low Temperature Hyperthermia System realizes many advantages over the existing art:

It is no longer necessary to pre-image to ensure the nano-particles are in the correct location since the temperature rise is limited to a safe 42° C. Healthy tissue is not harmed even if a nano-particle errantly resides in a healthy cell.

The targeting capability of multi-dimensional radiation technology enables the exact shape of the tumorous region plus some extended boundary volume to be treated with radiation. This precision is difficult with other types of treatment technologies.

The Low Temperature Hyperthermia System realizes up to three stepped methods of cancer cell killing: radiation and/or chemotherapy, low temperature hyperthermia, and cytotoxin. This ensures a very high kill rate and significantly lowers the probability that the cancer will reappear after treatment.

Cancer cells that may have realized a low nano-particle uptake concentration can be further treated with a cytotoxin. This is of particular use when the cancer is of a more deadly variety or if it is known that the uptake of a given cancer cell for a given nano-particle type is naturally low.

If for some reason nano-particles cannot be used for a given patient, it is possible to use RF- or microwave-based hyperthermia without particles but with very tight temperature feedback controls for the second level of treatment to realize the target 42° C. in the cancerous tissue and surrounding tissue. In this case, there is no temperature discrimination between cancer and healthy tissue in terms of heating. This approach isn't optimal, since heating fields can cause hot spots, such as in healthy tissue, but it is a fallback if nano-particles can't be used.

Tumors in any location, ranging from on or near the skin to deep in the abdomen or lungs, can be treated easily and safely.

Nano-particles are safely removed by the body's natural filtering systems after radiation and field treatment is complete. Thus, residual nano-particles do not stay in the body.

At 42° C., Heat Shock Protein production is reduced, thereby minimizing the level of cancer stem cells/other cells emitted by the resident cancer.

This Low Temperature Hyperthermia System takes advantage of many treatment modalities, each having distinct advantages, wherein the combined treatment protocol is safe and efficacious. The combined approach of multiple killing steps can be optimized further based on the specifics of a given cancer and the individual. This level of flexibility and control has heretofore not been available. The approach taken is one of optimizing the relationship between the exciting energy field and the nano-particle characteristics, where the optimization is in this case one of behavior at a given specified temperature. Certain properties are designed into the nano-particles to enable a pre-determined, pre-designed a priori temperature rise based on the strength of the illumination energy field: E, H, E and H, or EM.

Figure 20:
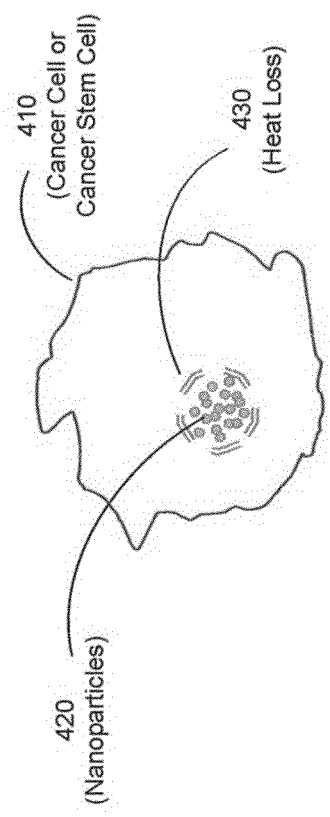
FIG. 20 illustrates a typical cancer cell which has a plurality of nano-particles implanted within the cancer cell.

In FIG. 20, a cancer cell 410 has a locus of nano-particles resident 420. When the nano-particles 420 are heated by the external illumination energy field, a heat transfer loss occurs at 430 between the nano-particles and the cancer cell. In order to realize an optimal temperature distribution across the cancer cell's extent, where such temperature profile is somewhat dependent on whether the nano-particles have clumped in the cancer cell, the target temperature of the nano-particle could be the same as the target temperature of the cancer cell or it could be different to account for the thermal loss between the nano-particles and the cancer cell. In this example, the nano-particles are heated to a temperature higher than that of the cancer cell due to a thermal loss at the particle/cell interface, where the heat loss is shown as 430. To determine the particle temperature, the desired cancer cell temperature and the loss parameters are determined. In this example, the desired cancer cell temperature is 42° C., and that is equivalent to the nano-particle temperature minus the temperature loss.

Methods of Controlling Nano-Particle Temperature

There are at least three methods for accurately controlling the nano-particle temperature: the Curie temperature, the magneto-caloric effect, and the electro-caloric effect. As shown in FIG. 15, there are minimally four attributes of interest: the Effect (450), the Field Type (460), the Field Dependence (470), and the Temperature Dependence (480). For the Effects (450), there are minimally three approaches to realize a controlled temperature rise in a nano-particle: the Magneto-caloric Effect (451), the Electro-caloric Effect (452), and the Curie Temperature (453). Now, looking horizontally, the attributes of each Effect can be studied. For the magneto-caloric effect, the field type is Magnetic (461) and the field dependence is Field Strength (471) with temperature dependence on H-Field Strength (481). Similarly, for the electro-caloric effect, the field type is Electric (462) with the field dependence being Field Strength (472), and the temperature dependence on E-Field Strength (482). Last of the three, Curie temperature, has a field type of Magnetic (463) with a field dependence of a Field Strength Cut-off (473), and a temperature dependence of a given H-Field strength and nothing higher.

Alternatively, it is possible to use a heating method where "regular" nano-particles that heat up in a field, whether the field is electric or magnetic or a combination of the two, are used to heat up cancer cells. This approach does not have the precision of using specially designed nano-particles. Some feedback mechanism must be employed to accurately manage the applied energy field to not exceed the desired cancer cell temperature. This is a very complex process, albeit not impossible, that requires some way of accurately measuring the cancer cells' temperature. The field excitation must be anticipated to not overshoot the heating of the cancer to a non-Low Temperature Hyperthermia range. For cancers other than skin cancer, this could be very complex and ultimately not very accurate.

Magneto-Caloric Effect in the Low Temperature Hyperthermia System

The magneto-caloric effect was originally envisioned for magnetic cooling or refrigeration. Since the magneto-caloric effect's cooling stage happens after the magnetic field is removed, it can be used to bring substances very close to absolute zero (after the initial ambient heat rise is removed by other environmental cooling means). This is called adiabatic demagnetization. While at the moment we do not anticipate using the cooling phase of magnetic refrigeration for cancer treatment, it is certainly available to us as part of this system (presently not used but claimed herein).

The magneto-caloric effect heating during the adiabatic magnetization phase is due to the application of a Direct Current (DC) magnetic field. This is in contrast to the heating of ferromagnetic particles in an Alternating Current (AC) magnetic field. This is an important distinction between the multiple methods described herein which are used to heat nano-particles to a given temperature; magneto-caloric is a DC magnetic field, while particles in the ferromagnetic state are best heated using an AC magnetic field.

What is of particular interest to the cancer treatment envisioned herein is the precise rate of temperature rise when magneto-caloric materials are subjected to a magnetic field of given strength, measured in Amps per Meter. While "regular" nano-materials such as iron ferrite $Fe_3O_4$ heat in an Alternating Current magnetic field, where the frequency of the magnetic field varies from hundreds of kilohertz to megahertz, the rate of rise is less precisely correlated to magnetic field strength. For iron ferrite in a high frequency magnetic field, the nano-particle does heat, and the heating is correlated to magnetic field strength, it is not specifically correlated to a set number of degrees of temperature rise for a given increase in magnetic field strength (such as the case for magneto-caloric nano-particles in a DC field of a given field strength). For iron ferrite, the linear, squared, or cubed relationship to the magnetic field is prevalent as it relates respectively to being in the Brownian, Neel, or Rayleigh magnetic regions (Rayleigh can be both squared and cubed, variable dependent). Thus, an iron ferrite particle could be used, but it does not have the precise heating characteristics of a magneto-caloric nano-particle.

Certain materials exhibit the magneto-caloric effect. One such chemical element is gadolinium, which is also used in an alloy form as a contrast agent in Magnetic Resonance Imaging (MRI). Thus, this material is safe for use in humans and simply needs to be processed in nano-meter dimensions. The gadolinium alloy $Gd_5(Si_2Ge_2)$ has a much stronger magneto-caloric effect. Praseodymium alloy with nickel $PrNi_5$ has a very strong magneto-caloric response, so strong that it has enabled temperatures to within one thousandth of a degree of absolute zero. This particular "cooling" application is somewhat different from the approach described herein.

The Low Temperature Hyperthermia System uses the Adiabatic Magnetization stage of magnetic cooling, wherein the nano-particles exhibiting a magneto-caloric effect residing in a cancer cell then are exposed to a magnetic field with specific field strength. This field strength is determined a priori for the given particle's material composition based on a specified desired temperature rise. The magnetic field causes the magnetic dipoles of the atoms to align, which means the particle's magnetic entropy must decline (go down). Since no energy is lost yet, thermodynamics teaches us that the nano-particles' temperature must go up. It is this very tightly controlled temperature rise, based on a given magnetic field strength, which is of great interest in realizing Low Temperature Hyperthermia.

Clearly, for the cancer cell treatment application of Low Temperature Hyperthermia, what is desired is a nano-particle fabricated from a material that offers around 5° C. to 10° C. of temperature rise in a reasonable magnetic field. Since the normal temperature of the human body is around 37° C., to reach a nominal cellular target temperature of 42° C. plus some heat loss, the nano-particle must be capable of a 5° C. to 10° C. temperature rise in a specified magnetic field. For example, 37° C. ambient body temperature plus 10° C. of nano-particle temperature rise yields a nano-particle temperature of 47° C. Then subtract 5° C. of thermal loss in this example to yield a cancer cell temperature of 42° C. Other levels of thermal loss are possible and are used in this document as other examples of how this system works.

Figure 16:
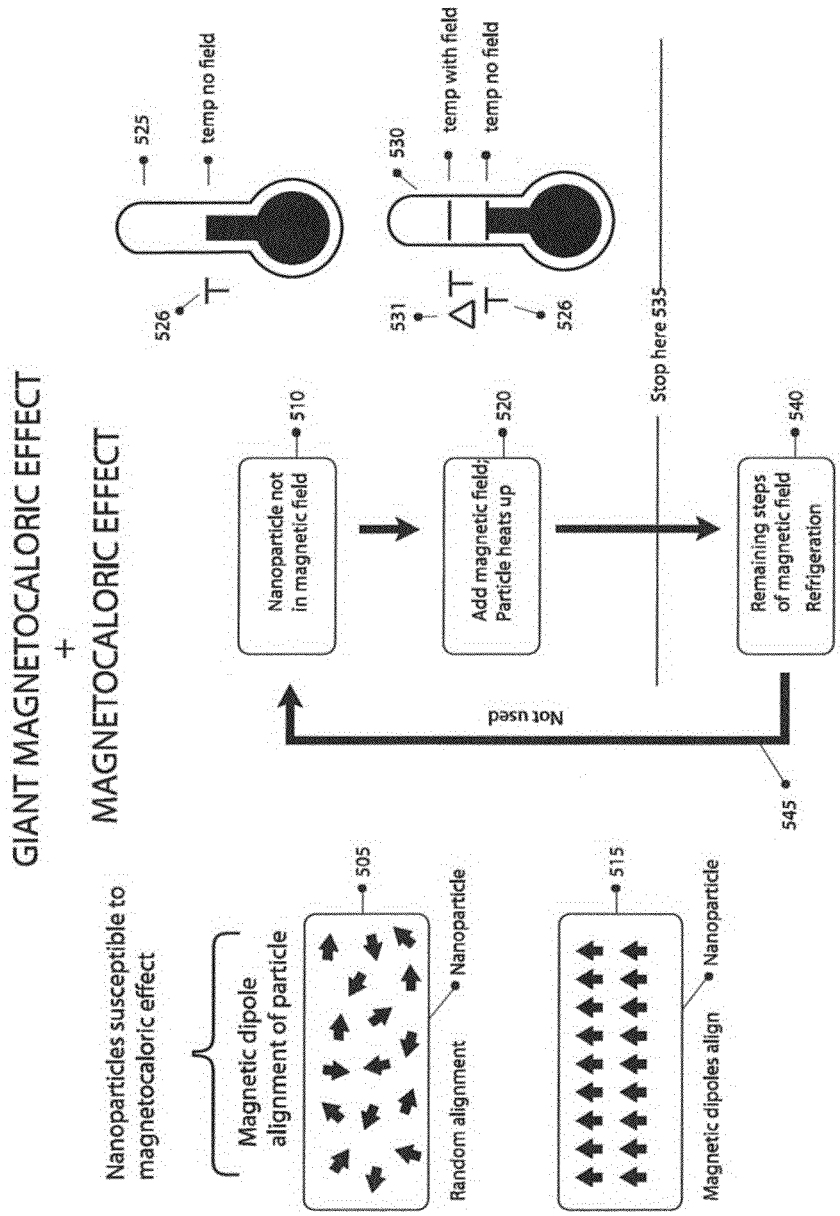
FIG. 16 illustrates the Magneto-caloric Effect nano-particle temperature effect when in a magnetic field.

For the Magneto-caloric Effect', as shown in FIG. 16, nano-particles are designed to exhibit this effect at the desired field strength and per degree temperature rise correlation. As illustrated in element 505, the magnetic dipoles of the nano-particle exhibit random alignment when not in the presence of a magnetic field. As illustrated in element 515, when exposed to a magnetic field, the magnetic diploes of the nano-particle align, and nano-particle heating occurs at a specified rate per the applied magnetic field strength; the rate of heating is measured in degrees per incremental field of some value. The process described herein uses a portion of the magnetic refrigeration cycle and discards the unneeded steps of the cycle. Thus, at step 510, the nano-particles are located in the cancer cell but are not in a magnetic field; the magnetic field is off. Thus, the particle temperature is at ambient, which is the temperature of the cancer cell. This is illustrated in elements 525 and 526. When the magnetic field is applied to the cancerous region, the nano-particles in the cancer cells have their magnetic dipoles align at step 520. The temperature rise is specified by the Magneto-caloric Effect's properties, and the rise is shown at level 531 as illustrated in element 530 (ambient temperature was level 526). The Low Temperature Hyperthermia System achieves a tightly controlled thermal rise based on the magnetic field's exciting strength at the region or locus of the cancer cells where the nano-particles reside under the precise control of the system. Since the remaining steps are the magnetic refrigeration process, the process terminates at step 535, and steps 540 and 545 are not executed.

For room temperature adiabatic magnetization heating, a number of materials exhibit properties of interest; most are alloys of gadolinium. This is advantageous since gadolinium alloys are being used as contrast agents for MRIs, meaning the material has been approved for use in humans. Gadolinium is strongly paramagnetic at room temperature and exhibits ferromagnetic properties below room temperature. It's Curie temperature, as a pure element, is 17° C.-above 17° C., gadolinium is paramagnetic, meaning it only has magnetic properties when it is placed in a magnetic field (the magnetic spins or dipoles are random until a magnetic field is applied). Alloys of gadolinium may have different Curie points. Gadolinium exhibits a magneto-caloric effect where its temperature rises when placed in a DC magnetic field, and the temperature decreases when it is removed from the DC magnetic field.

Electro-Caloric Effect in the Low Temperature Hyperthermia System

Similarly, for the Electro-caloric Effect, when a specially designed nano-particle which exhibits an Electro-caloric Effect is placed in a DC electric field, the temperature rise of the nano-particle is dependent on the field strength of the electric field Like the magnetic cooling cycle, the Low Temperature Hyperthermia System 150 uses the first steps of the process and does not use the remaining cooling steps Like the Magneto-caloric Effect with magnetic fields, the Electro-caloric Effect realizes a specified temperature increase when exposed to an electric field. As an example material, PZT, a mixture of oxygen, zirconium, lead, and titanium with a 12° C.-temperature response in a field voltage as low as 25 volts was used; the ambient temperature in this example was 220° C. At room temperature, ferroelectric polymers have shown 12° C. of temperature change when exposed to a DC electric field. Sometimes this effect is called the Giant Electro-caloric Effect.

Figure 17:
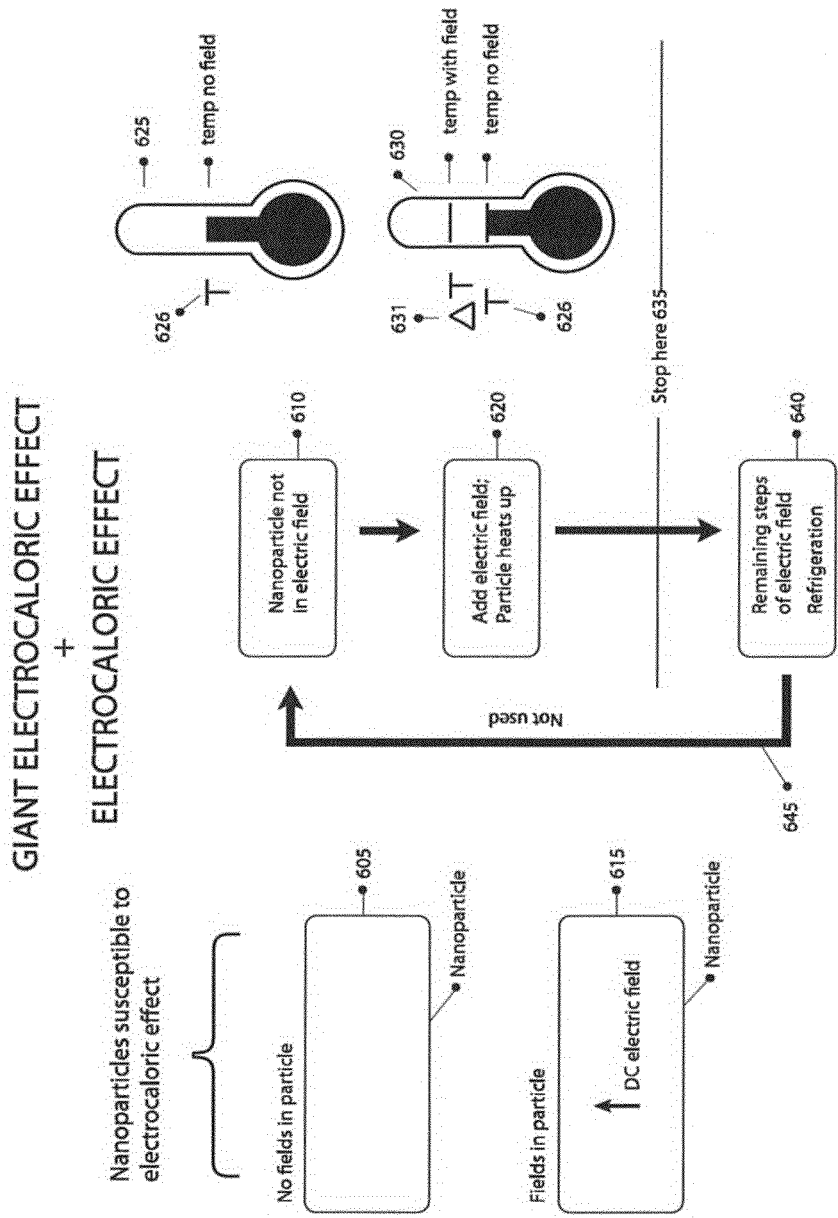
FIG. 17 illustrates the Electro-caloric Effect nano-particle temperature effect when in an electric field.

FIG. 17 shows the Electro-caloric Effect. As illustrated in element 605, a nano-particle is shown not in an electric field, while the nano-particle is illustrated in element 615 as in the electric field. At step 610, the nano-particle is not in the DC electric field and has an ambient temperature of level 626 as illustrated in element 625. When the DC electric field is applied to the nano-particle at step 620, the temperature rises to ΔT at level 631 which is greater than the ambient temperature of T at level 626 (is illustrated in element 630). The remaining steps of the Electro-caloric cooling process, steps 640 and 645, are not used and the process stops at step 635. Of course, like the magnetic cooling process, the electric cooling process has additional steps which offer cooling to cancer cells—for now, only heating is desired.

Figure 18:
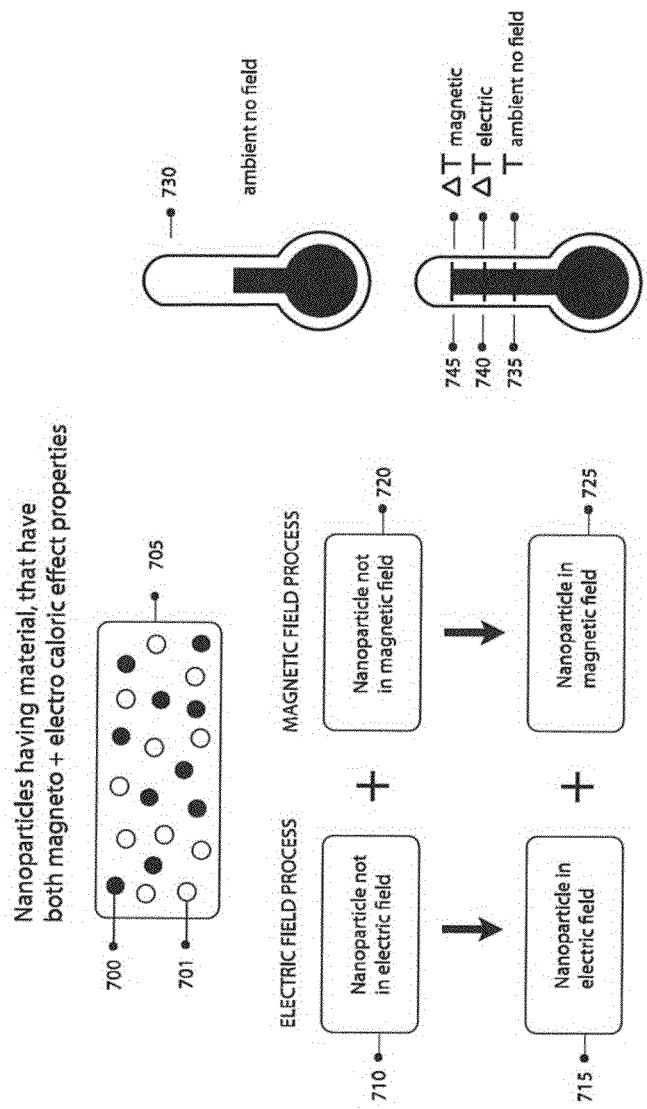
FIG. 18 illustrates the combined Magneto-caloric and Electro-caloric Effect effects.

Combined Magneto- and Electro-Caloric Effect in the Low Temperature Hyperthermia System FIG. 18 illustrates the use of a nano-particle 705 that is susceptible to both Magneto-caloric 700 and Electro-caloric 701 Effects. When the nano-particle is located in the body and is not in an electric field as illustrated in element 710 and not in a magnetic field as illustrated in element 720, the ambient temperature of level 735 (T) is realized. When the nano-particle is illuminated by an electric field as illustrated in element 715 and a magnetic field as illustrated in element 725, the corresponding temperature rise in the nano-particle has two components, one from the electric field nano-particle response as indicated by level 740 $\Delta T_{Electric}$ and the second from the magnetic field response as indicated by level 745 $\Delta T_{Magnetic}$. These two responses create or enable a "doubling" of the temperature rise over the ambient temperature. Both of these fields, magnetic and electric, are DC in nature.

Curie Temperature

The Curie temperature of a material is the physical temperature where the material transitions from a ferromagnetic state to a paramagnetic state. Below the Curie temperature, the material is ferromagnetic; above the Curie temperature, the material is paramagnetic. This means that the magnetic dipoles or spins of the atoms of the material go from an aligned, ordered state (ferromagnetic) to a purely random state (paramagnetic) (in the absence of an applied magnetic field). This effect is reversible in certain materials as the material moves back and forth across, or above and below, the Curie temperature.

Above the Curie temperature, the thermal energy overcomes the ion magnetic moments resulting in disordered or random magnetic dipoles (the spins) and the material is no longer ferromagnetic. It is now paramagnetic. Paramagnetic materials, in absence of a magnetic field, do not exhibit any magnetic effect. Paramagnetic materials, even in the presence of a magnetic field, only have a relatively small induced magnetization because of the difference between the number of spins aligned with the applied field and the number of spins aligned in the opposing direction.—Only a small percentage of the total number of spins are oriented by the field flux lines.

How does a nano-material behave when in a magnetic field when the temperature is above the Curie point and it is now paramagnetic? This depends on whether the magnetic field is AC or DC. Below the Curie temperature, a ferromagnetic material in an Alternating Current (AC) magnetic field results in nano-particle heating. This is due to the "forced" alignment and re-alignment of the magnetic dipole with the phase of the magnetic field; as the phase changes with time (AC), the dipole attempts to re-align. This creates heating in the ferromagnetic nano-particle. If this field were DC, or a static magnetic field, no steady state heating occurs.

Above the Curie temperature, the material is now paramagnetic. This means the magnetic dipoles are random in the nano-particle. When placed in a DC field, no steady state heating occurs. When placed in an AC or Alternating Magnetic field, there is only a small fraction of the magnetic dipoles or spins that are affected, meaning the "induced" magnetization is low. This is proportional (linear) to the applied field strength. Since the magnetic dipole re-ordering is not anywhere near the magnitude of the magnetic dipole re-ordering in a ferromagnetic particle in an AC magnetic field, the heating of a paramagnetic material past its Curie temperature is considerably less.

Some paramagnetic materials are also Magneto-caloric, but only a few. Magneto-caloric materials are paramagnetic with special behavior associated with being Magneto-caloric. This should not be confused with materials that are hotter than their Curie temperature and have now become paramagnetic. This particular paramagnetic state is not Magneto-caloric.

Magnetic materials of a certain design exhibit a Curie temperature effect wherein, after a certain magnetic field strength is realized, the material (or nano-particle in this case) no longer continues to heat. Paramagnetic materials, even in the presence of a magnetic field, only have a relatively small induced magnetization because of the difference between the number of spins aligned with the applied field and the number of spins aligned in the opposing direction is only a small percentage of the total number of spins. The paramagnetic spins still align along the field lines, but there are not that many that have to be flipped when the field direction is reversed.

Figure 19:
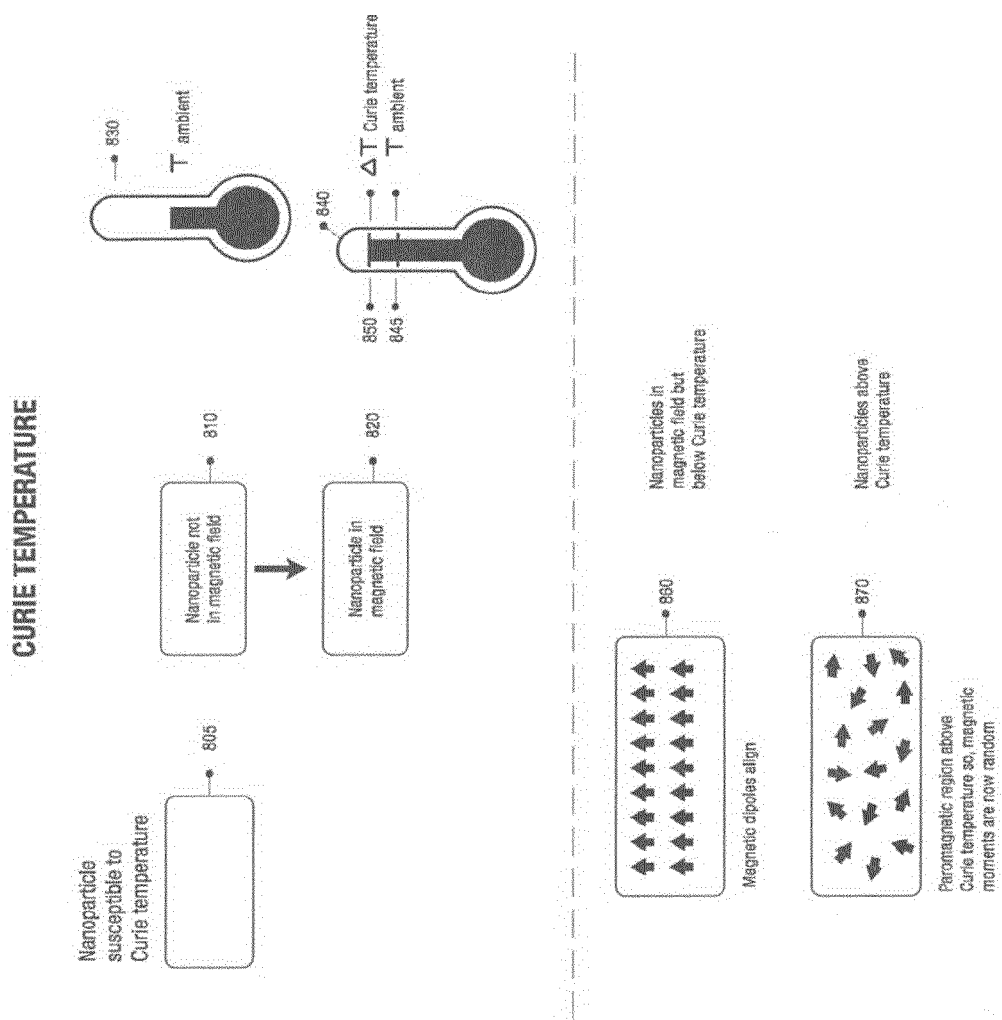
FIG. 19 illustrates the Curie temperature effect when nano-particles are situated in a magnetic field.

FIG. 19 illustrates the Curie temperature effect when nano-particles are situated in a magnetic field, where elements 860 and 870 are illustrative of this process. Element 870 illustrates that past the Curie temperature the spins of the magnetic material of the nano-particles are not aligned and the domains are random in nature. At 860, the dipoles are aligned even without an applied magnetic field; and element 860 is meant to illustrate the effect of adding a magnetic field. The temperature where this occurs is material dependent and, thus, can be designed to occur at specific temperatures, thereby offering a means to precisely control cancer cell heating. As illustrated in element 805, a nano-particle is shown which is susceptible to heating as a result of being exposed to a magnetic field. As illustrated in element 810, the nano-particle is not in the magnetic field (i.e., the field is turned off) and the nano-particle temperature is stable with its ambient surroundings as illustrated in element 830. For the nano-particle that has been introduced into a cancer cell, this temperature is approximately the ambient body temperature of 37° C. (as illustrated in element 830). When a magnetic field is applied as illustrated in element 820, the nano-particle heats until the Curie temperature is reached wherein the heating essentially stops. This is illustrated as level 850 in element 840. The ambient temperature of level 845 is elevated to a new temperature of level 850, which shows the temperature rise due to the Curie temperature of the nano-particle material.

Thermal Response to Low Temperature Hyperthermia System

The Magneto-caloric Effect example discussed next has the body temperature at 37° C., the nano-particle at 44.5° C., and having thermodynamic losses of 2.5° C. to produce the resultant temperature in the cancer cell of 42° C. This value of 42° C. resides in the Low Temperature Hyperthermia range and is highly desirable for reasons stated herein to include the minimization of the release of cancer stem cells. Gadolinium has been shown to have a strong Magneto-caloric Effect with 21° C. of temperature change starting at room temperature or around 21° C. (70° F.). Gadolinium has been shown to support up to 60° C. of temperature change. In the Magneto-caloric example, the magnetic nano-material rises 1.5° C. per 3 kA/m of magnetic field. By using the temperatures just discussed, we need 7.5° C. of temperature rise over ambient. This means that the magnetic field needed is 15 kA/m, as shown in the following calculation:

(7.5° C.*3 kA/m)/1.5° C.=15 kA/m

An Electro-caloric effect example is next with the same temperature ranges as the magnetic example, where the temperature here is a function of the electric field and the nano-particle material. The target cancer cell temperature is 42° C. and a nano-particle exhibiting 2° C. temperature rise per 0.75 kV/m electric field strength requires a total DC electric field strength of 2.81 kV/m in order to realize the desired particle temperature rise of 7.5° C. as shown in the following calculation:

(7.5° C.*0.75 V/m)/2.0° C.=2.81 kV/m

This raises the temperature of the nano-particle from an ambient temperature of 37° C. to 44.5° C. less 2.5° C. of loss to arrive at the target temperature of 42° C. for the cancer cells. An example Electro-caloric material is a ferroelectric polymer which has up to 12° C. of temperature change at room temperature.

Last is an example to illustrate the Curie Temperature process. At a temperature of 44.5° C., it is desired to have the nano-particle heating largely stop at the Curie point of 44.5° C. The nano-material is selected to have this temperature characteristic. Thus, for example, the magnetic field strength (DC) may be raised to 25 kA/m, even though the Curie point is reached with a magnetic field of 20 kA/m. This small overage of field strength insures that the Curie point is reached for all particles, and the target particle temperature of 44.5° C. is realized. The additional field strength from 20 to 25 kA/m does not cause significant temperature rise above the Curie temperature of 44.5° C. Subtract 2.5° C. of heat loss, and the target cancer cell temp of 42° C. is realized. Example Curie temperatures for selected nano-particle materials include: chromium bromide=37° C.; europium oxide=77° C.

Arrhenius Curve for Low Temperature Hyperthermia

It is important to stay in the 42° C. to 42.25° C. temperature range or cooler as shown in FIG. 10, lines 1030. Note the cell death rate is very small for this Low Temperature Hyperthermia range. At 42° C., the probability of cell death almost flattens out and is relatively independent of time. In contrast, the cell death rate at 46.5° C. is almost vertical, meaning cell death occurs almost instantaneously. Thus, in just a 4.5° C. span, the cell death rate goes from virtually zero to 100%. Thus, it is paramount that the cellular temperature be tightly controlled-; and be targeted at 42° C. or less. Observe how dramatic the cell death rate is from 42.0° C. to 43.0° C. This underscores how important tight temperature control is and, correspondingly, how critical the particle design is in conjunction with the applied field strength. Being off by even as much as 1.0° C. causes this process to fail. Thus, designing the temperature control largely into the material properties of the nano-particle is the critical inventive step necessary for success.

The Arrhenius curve is independent of whether the cells are in vivo (in the body) or in vitro (in the glass). Thermodynamic equations which describe the heat loss from the nano-particles, whether the nano-particles are clumped in the cancer cell or whether the nano-particles are evenly distributed in the cancer cell, enable the incorporation of heat loss to determine the optimal particle temperature. The physiological benefits of Low Temperature Hyperthermia, primarily the minimization of the release of cancer stem cells, require that the temperature range stay at 42° C. and cooler. Certain conditions affect the positioning of the Arrhenius curve and include acidification or step down hyperthermia and post thermal tolerance induction. These also need to be considered for a given patient treatment protocol.

Benefits of Low Temperature Hyperthermia

The benefits of Low Temperature Hyperthermia are realized between the temperature range of 41° C. to 41.5° C. in skin. The optimal temperature is different for different tissue types, and this description has used the target temperature of 42° C.; but in practice, this temperature could be anything that is optimal for a given tissue type.

Of note, cancer cells can adapt to heat stress by becoming thermo-tolerant. This is caused by the release of Heat Shock Proteins. Thermo-tolerance tends to shift the Arrhenius curve down and to the right, indicating higher temperatures are needed along with greater times at that temperature to realize the same effect. Thus, minimizing the level of Heat Shock Proteins reduces the level of resistance to hyperthermia treatment. Low Temperature Hyperthermia has a number of beneficial effects: it improves perfusion where skin perfusion can be 10-fold while tumor perfusion can be 1.5- to 2.0-fold. Increased blood vessel pore size is realized, where both of these effects improve drug delivery performance, such as via liposomes (lipid). Increased profusion and blood vessel size also enhance re-oxygenation 1380, which is critical since cancer stem cells prefer a hypoxic environment. Thus, this helps kill cancer cells. Enzymes for aerobic metabolism are more heat sensitive than those for anaerobic metabolism. Thus, during Low Temperature Hyperthermia, there is a concomitant reduction in tumor respiration. Respiration inhibition is caused by this process. Minimizing the level of heat shock proteins is important since cancer cells with Heat Shock Proteins are relatively resistant to hyperthermia treatment. In addition, acute acidification of cancer cells below their resting pH leads to catastrophic cell death.

SUMMARY

The Invasive Agent Treatment System provides the necessary coordination among the characteristics of the nano-particles, concentration of nano-particles, duration of treatment, and applied fields to enable the generation of precisely crafted fields and their application in a mode and manner to be effective with a high degree of accuracy.

What is claimed as new and desired to be protected by Letters Patent of the United States is:

1. A method for dynamically defining characteristics of generated energy fields which are used in activating target particles, which are inserted into a living organism in a manner to associate with invasive agents, to destroy invasive agents in the living organism, comprising:
   maintaining, in a computerized target particle database, a listing of characteristics of at least one type of target particles;
   storing, in a computerized invasive agent database, data that defines sets of energy field characteristics from the characteristics of energy fields including, but not limited to, at least one of: field type, frequency, field strength, duration, field modulation, repetition frequency, polarization, beam size, and focal point, each set defining the energy field characteristics necessary to energize the at least one type of said target particles in a predetermined manner in a portion of the living organism to destroy the invasive agent;
   automatically selecting, using user provided identification of the at least one type of said target particles and a portion of the living organism which contains an invasive agent, a set of energy field characteristics as stored in the computerized invasive agent database, necessary to energize the identified type of target particles in a predetermined manner in the portion of the living organism to destroy the invasive agent; and
   generating an energy field having said automatically selected energy field characteristics for application to said portion of said living organism to activate said target particles located in the living organism to destroy invasive agents in the target living organism.

2. The method for dynamically defining characteristics of generated energy fields of claim 1 wherein said step of automatically selecting differentially heats said portion of said target living organism by selecting a frequency of said energy field which energizes the identified type of target particles to a temperature that is greater than the temperature of living tissue which surrounds said portion of the living organism which contains the invasive agent.

3. The method for dynamically defining characteristics of generated energy fields of claim 2 wherein said step of automatically selecting linearly decreases the field strength of an E-Field as the frequency of the E-Field increases to deliver a substantially constant power to the identified target particles.

4. The method for dynamically defining characteristics of generated energy fields of claim 3 wherein said step of automatically selecting selects an E-Field strength where the power absorbed at the identified target particles is a function of the E-Field strength squared.

5. The method for dynamically defining characteristics of generated energy fields of claim 2 wherein said identified type of target particles have a relative permittivity which is a complex value, having both real and imaginary portions, where the imaginary portion of the permittivity changes with frequency and determines a loss a given material has in an E-Field, said step of automatically selecting adjusts the E-Field strength as a function of frequency.

6. The method for dynamically defining characteristics of generated energy fields of claim 2 wherein said identified type of target particles have a permittivity and polarity which are temperature dependent, and said step of automatically selecting dynamically changes the E-Field strength during the heating of the identified type of target particles.

7. The method for dynamically defining characteristics of generated energy fields of claim 2 wherein said step of automatically selecting selects an energy field strength as a function of target particle radius cubed for E-Fields and target particle radius to the fifth power for H-Fields.

8. The method for dynamically defining characteristics of generated energy fields of claim 1 wherein said identified type of target particles are made of material types responsive to both magnetic and electric fields, and said step of automatically selecting illuminates the target particles with a magnetic field and an electric field.

9. The method for dynamically defining characteristics of generated energy fields of claim 1 wherein said step of automatically selecting linearly decreases the field strength of an E-Field as the frequency of the E-Field increases to realize a substantially constant power absorbed by the identified type of target particles.

10. The method for dynamically defining characteristics of generated energy fields of claim 9 wherein said step of automatically selecting is selects an E-Field strength where the power absorbed by the identified type of target particles is a function of the E-Field strength squared.

11. The method for dynamically defining characteristics of generated energy fields of claim 9 wherein said identified type of target particles have a relative permittivity which is a complex value, having both real and imaginary portions, where the imaginary portion of the permittivity changes with frequency and determines a loss a given material has in an E-Field, and said step of automatically selecting dynamically adjusting adjusts the E-Field strength as a function of frequency.

12. The method for dynamically defining characteristics of generated energy fields of claim 9 wherein said identified type of target particles have a permittivity and polarity which are temperature dependent, and said step of automatically selecting dynamically changes the E-Field strength during heating of the identified type of target particles due to the application of the generated energy field.

13. The method for dynamically defining characteristics of generated energy fields of claim 9 wherein said step of automatically selecting selects an energy field strength as a function of target particle radius cubed for E-Fields and target particle radius to the fifth power for H-Fields.

14. The method for dynamically defining characteristics of generated energy fields of claim 1, further comprising:

maintaining a target particle location database for storing data indicative of a presence and locus of target particles which are located in a living organism.

15. The method for dynamically defining characteristics of generated energy fields of claim 1, further comprising:

maintaining destruction databases for storing data relevant to destruction of invasive agents, comprising at least one of:

a target particle location database for storing data indicative of a presence and locus of target particles which are located in a living organism, a patient data database for maintaining living organism-specific data which provides data regarding at least one of: age, sex, weight, prior surgeries, or other conditions relevant to destruction of invasive agents, an empirical and analytical data database for maintaining information, which has been collected via at least one of: modeling, testing, theoretical computations, and past experiences, relating to destruction of invasive agents in a living organism, a reflection characteristics database for maintaining data which represents a percentage of an incident signal which is reflected at an interface between two materials, a penetration depth database for maintaining data which represents an attenuation of an incident signal as it passes through a selected material, and a living organism characterization database for storing data which defines a three-dimensional physical composition of at least one characteristic of a living organism selected from the set of characteristics comprising: material, shape, size, density, and surface treatment.

16. The method for dynamically defining characteristics of generated energy fields of claim 15 wherein said step of automatically selecting comprises:

determining, in response to said data stored in said destruction databases, characteristics of an energy field, incident on said identified type of target particles, required to activate said identified type of target particles located in the living organism to respond in a predetermined detectable manner to destroy invasive agents in the living organism by raising the temperature of the invasive agent due to the application of the generated energy field to the identified type of target particles.

17. The method for dynamically defining characteristics of generated energy fields of claim 16 wherein said step of automatically selecting comprises:

correlating said determined characteristics of an energy field with empirical and analytical data maintained in said empirical and analytical data database to generate refined determined characteristics.

* * * * *